(12) United States Patent
Shepherd et al.

(10) Patent No.: US 7,075,628 B2
(45) Date of Patent: Jul. 11, 2006

(54) METHOD AND APPARATUS FOR DIRECT SPECTROPHOTOMETRIC MEASUREMENTS IN UNALTERED WHOLE BLOOD

(75) Inventors: A. P. Shepherd, San Antonio, TX (US); John M. Steinke, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 216 days.

(21) Appl. No.: 10/313,220

(22) Filed: Dec. 6, 2002

(65) Prior Publication Data

US 2003/0202170 A1    Oct. 30, 2003

Related U.S. Application Data

(63) Continuation of application No. 09/902,823, filed on Jul. 10, 2001, now Pat. No. 6,519,025, which is a continuation of application No. 07/953,680, filed on Sep. 29, 1992, now Pat. No. 6,262,798, which is a continuation-in-part of application No. 07/313,911, filed on Feb. 23, 1989, now abandoned.

(51) Int. Cl.
*G01N 33/48* (2006.01)
*G01N 21/00* (2006.01)

(52) U.S. Cl. .......................... 356/40; 356/39; 356/432

(58) Field of Classification Search ................ 356/39, 356/40, 41, 42, 409, 436, 442; 250/573, 250/574
See application file for complete search history.

(56) References Cited

U.S. PATENT DOCUMENTS

| | | | |
|---|---|---|---|
| 2,878,715 A | 3/1959 | Rhees | |
| 3,296,922 A | 1/1967 | Goldberg | |
| 3,516,746 A | 6/1970 | Shibata et al | |
| 3,527,542 A | 9/1970 | Penhasi et al | |
| 3,638,640 A | 2/1972 | Shaw | |
| 3,692,410 A | 9/1972 | Jurany et al | |
| 3,764,267 A | 10/1973 | Farr | |

(Continued)

FOREIGN PATENT DOCUMENTS

EP        0 210 417 B1    6/1986

OTHER PUBLICATIONS

Anderson, et al., "Light-Absorbing and Scattering Properties of Non-Haemolysed Blood," *Phys Med. Bio.*, 12 (2):173-184, 1967.

(Continued)

*Primary Examiner*—Layla G. Lauchman
(74) *Attorney, Agent, or Firm*—Fulbright & Jaworski

(57) ABSTRACT

A method and apparatus that allows accurate spectrophotometric determination of the concentrations of various hemoglobin species in whole undiluted blood. The invention employs 1) an optical apparatus designed to maximize the true optical absorbance of whole blood and to minimize the effects of light scattering on the spectrophotometric measurements of the concentrations of various constituent components, and 2) methods to correct the hemoglobin concentration measurements for light scattering and for the effects of the finite bandwidth of the substantially monochromatic light. In the optical apparatus optical parameters, such as sample thickness, detector size and shape, sample-to-detector distance, wavelengths, monochromicity, and maximum angle of light capture by detector, are selected so as to minimize the contribution of light scattering to maximize the contribution of true optical absorbance. After making measurements of a blood sample's optical density at each of the wavelengths, corrections are made for the effects of light scattering.

2 Claims, 14 Drawing Sheets

U.S. PATENT DOCUMENTS

| | | | |
|---|---|---|---|
| 3,799,672 | A | 3/1974 | Vurek |
| 3,972,614 | A | 8/1976 | Johansen et al. |
| 3,994,585 | A | 11/1976 | Frey |
| 4,003,662 | A | 1/1977 | Retzer et al. |
| 4,013,417 | A | 3/1977 | Raffaele |
| 4,057,394 | A | 11/1977 | Genshaw |
| 4,134,678 | A | 1/1979 | Brown et al. |
| RE30,007 | E | 5/1979 | Steuer et al. |
| 4,240,749 | A | 12/1980 | Retzer |
| 4,243,883 | A | 1/1981 | Schwarzmann |
| 4,301,412 | A | 11/1981 | Hill et al. |
| 4,303,887 | A | 12/1981 | Hill et al. |
| 4,308,029 | A | 12/1981 | Siggaard-Andersen |
| 4,324,556 | A | 4/1982 | Robertson et al. |
| 4,357,105 | A | 11/1982 | Loretz |
| 4,444,498 | A | 4/1984 | Heinemann |
| 4,453,266 | A | 6/1984 | Bacus |
| 4,502,786 | A | 3/1985 | Golias et al. |
| 4,565,448 | A | 1/1986 | Abbott et al. |
| 4,605,305 | A | 8/1986 | Lenoir et al. |
| 4,651,741 | A | 3/1987 | Passafaro |
| 4,700,708 | A | 10/1987 | New, Jr. et al. |
| 4,997,769 | A | 3/1991 | Lundsgaard |
| 5,064,282 | A | 11/1991 | Curtis ..................... 356/40 |

OTHER PUBLICATIONS

Drabkin, "The Crystallagraphic and Optical Properties of the Hemoglobin of Man in Comparison with Those of Other Species," *Spectrophotometric Studies*, 703-725, 1946.

Kiel, et al., "A Microcomputer Oximeter for Whole Blood," *Amer. J. Physiol.*, H722-H725, 1983.

Kramer, et al., "Influence of Oxygen Saturation, Erythrocyte Concentration and Optical Depth Upon the Red and Near-Infrared Light Transmittance of Whole Blood," *Amer. J. Physiol.*, 165:229-249, 1951.

Janssen, "A Study of the Absorption and Scattering Factors of Light in Whole Blood," *Med. Biol. Eng.*, 10:231-240, 1972.

Pittman, "In Vivo Photometric Analysis of Hemoglobin," *Annnals of Biomedical Engineering*, 14:119-137, 1986.

Pittman, et al., "A New Method for the Measurement of Percent Oxyhemoglobin," *Journal of Applied Physiol.*, 38 (2):315-3320, 1975.

Setsuo, et al., "A Miniature Hybrid Reflection Type Optical Sensor for Measurement of Hemoglobin Content and Oxygen Saturation of Whole Blood," *IEEE Transactions on Biomedical Engineering*, 35 (3):187-198, 1988.

Singh, et al., "Technical Note; Optical Method for Haemaocrit Determination," *Med & Biol. Eng. & Comput.*, 20:527-528, 1982.

Sinha, et al, "Blood $O_2$ Saturation Determination in Frozen Tissue," *Microvascular Research*, 14:133-144, 1977.

Steinke, et al., "Role of Light Scattering in Whole Blood Oximetry," *IEEE Transactions on Biomedical Engineering*, BME-33 (3):294-301, 1986.

Brochure Entitled, "OSM3 Hemoximeter, " Radiometer; Copenhagen, 1988.

PCT Search Report dated Nov. 12, 1993.

European Search Report; Ref. No. EP 11333-60.

METHOD AND APPARATUS FOR DIRECT SPECTROPHOTOMETRIC MEASUREMENTS IN UNALTERED WHOLE BLOOD

This is a continuation of prior application Ser. No. 09/902,823, filed Jul. 10, 2001, now U.S. Pat. No. 6,519,025 which is a continuation of prior application Ser. No. 07/953,680, filed Sep. 29, 1992, which issued on Jul. 17, 2001, as U.S. Pat. No. 6,262,798, which is a continuation-in-part of application Ser. No. 07/313,911, filed Feb. 23, 1989, now abandoned.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

This invention relates to a method and apparatus to assess the optical transmittance of a sample of unaltered whole blood at multiple wavelengths to attain an accurate measurement of its total hemoglobin concentration, the concentration of bilirubin, and the concentrations of oxy-, deoxy-, carboxy-, met-, and sulfhemoglobin.

BACKGROUND

To the best of the Applicants' knowledge, no prior art whether patented or not has ever successfully exploited the optical transmittance of unaltered whole blood to achieve an accurate measurement of the total hemoglobin concentration (THb) in a blood sample that could possibly contain as many as five different species of hemoglobin. Several different properties of whole blood have precluded such measurements. These characteristics include 1) the complex chemical mixture of as many as five individual hemoglobin species that are present in varying concentrations in a typical blood sample, and 2) the complex optical properties of whole blood that result from a combination of true optical absorbance by multiple light-absorbing compounds (including the hemoglobins, bilirubin, and other pigments), and the pronounced light-scattering ability of the red blood cells that are present in high concentrations.

Many prior methods have been devised to measure the total hemoglobin concentration in the complex chemical mixture of oxy-, carboxy-, met-, deoxy-, and sulfhemoglobin that comprise the total hemoglobin composition. For example, Loretz (U.S. Pat. No. 4,357,105) teaches a method whereby the hemoglobin is released from the red blood cells by the process of hemolysis, i.e. by disrupting the red blood cell membrane. Simultaneously, the various hemoglobin species are diluted by reagent solutions that convert them into a single chemical form, cyanmethemoglobin, the concentration of which is then measured spectrophotometrically by conventional apparatus.

FIG. 1 presents a graph of the extinction coefficients (indicative of optical absorbance) as a function of radiation wavelength for five individual hemoglobin species. Because the individual hemoglobin species differ significantly from each other in their optical absorbance spectra, no method that employs a single wavelength can measure the total hemoglobin concentration spectrophotometrically. Therefore, the chief advantage of the many prior methods that convert the sundry species into a single known species is that only one wavelength is needed for the subsequent spectrophotometric measurement of the resulting single species. The disadvantages of the above-mentioned chemical conversion methods are that 1) hemolysis and accurate dilutions are needed, 2) the reagents are often toxic, 3) chemical conversion is slow, 4) the red blood cells and the chemical nature of the whole blood sample are so drastically altered that the same sample cannot be used for further subsequent analyses of other blood constituents, and 5) the chemical conversion of the various hemoglobin derivatives into a single species makes it impossible to measure the original concentrations of the several individual species. The latter disadvantage is a serious limitation because the concentrations of oxy-, carboxy-, met-, deoxy-, and sulfhemoglobin provide valuable diagnostic information in many different medical applications.

In several patented methods (U.S. Pat. Nos. 4,134,678; 4,013,417; 3,972,614; and 4,997,769), the need for chemical conversion of the various hemoglobin derivatives into a single hemoglobin species has been eliminated by using multiple appropriate wavelengths to measure the concentration of each species. In such methods, the blood sample is either hemolyzed and diluted (Brown et al., U.S. Pat. No. 4,134,678; Raffaele, U.S. Pat. No. 4,013,417) or just hemolyzed (Johansen et al., U.S. Pat. No. 3,972,614; Lundsgaard, U.S. Pat. No. 4,997,769) to eliminate the light scattering by the red blood cells. The hemolyzed sample is then irradiated with at least one distinct wavelength for each of the three, four, or five hemoglobin species presumed to be present in the sample. By measuring the optical density of the hemolyzed sample with at least as many different wavelengths as there are unknown individual hemoglobin species, such methods yield a set of simultaneous equations that can subsequently be solved for the relative concentration of each of the various hemoglobin derivatives. These prior methods eliminate the need for chemically converting the various hemoglobin derivatives into a single species, but they suffer from the disadvantage of requiring a complex, bulky, and expensive apparatus comprised of pumps, plumbing, associated control circuitry, and in some cases, ultrasonic hemolyzers to dilute and hemolyze the blood sample. Finally, the techniques that employ hemolysis have two additional disadvantages: 1) their complicated plumbing systems are prone to clogging by blood residue, and 2) they aspirate and destroy the blood sample so that it cannot be retrieved and subjected to further analysis of other constituents.

In whole blood, the major obstacle to making optical measurements is the intense light scattering caused by the highly concentrated red blood cells, e.g. $5.4 \times 10^6$ RBCs/µl for human males. Consequently, all prior art has relied exclusively on hemolysis or on both hemolysis and dilution to reduce or eliminate the light scattering caused by red blood cells. This light scattering arises because the blood plasma and the red blood cells have different indices of refraction (B. Barer and S. Joseph, Quart. J. Microsc. Sci. 95:399,1954). Many uncontrollable factors make such light scattering unpredictable from one blood sample to another, including 1) the different plasma protein concentrations that determine the refractive index of plasma, 2) the aggregation and sedimentation of red blood cells in the sample, 3) the different hemoglobin concentrations inside the red blood cells that alter their refractive index, and 4) the size and shape of the red blood cells. The size and shape of the red blood cells differ from one animal species to another; they are also altered by disease states (e.g. sickle-cell anemia and spherocytosis); and they are altered by the osmotic pressure of the blood. Thus all prior methods which measure the total hemoglobin concentration and the relative concentrations of individual hemoglobin species have employed hemolysis to eliminate this intense, unpredictable light scattering caused by the red blood cells.

Prior art that relies on hemolysis to eliminate the intense light scattering by the red blood cells has the further disadvantage that even after thorough hemolysis the sample can be relatively turbid (L. R. Sehgal et al., Critical Care Medicine, 12:907–909, 1984). This residual turbidity in hemolyzed blood is small compared with the intense light scattering of red blood cells in unaltered whole blood (J. M. Steinke and A. P. Shepherd, *IEEE Trans. Biomed. Eng.* BME-33:294–301, 1986). Nevertheless, the residual turbidity in hemolyzed blood causes troublesome errors in the hemoglobin measurements. Thus, an additional disadvantage of prior apparatus that rely on hemolysis is the residual turbidity that results from a small number of unlysed red blood cells, lipid particles such as chylomicrons (a normal constituent of plasma that persists after hemolysis), light-scattering cell fragments produced by the hemolysis process, and other causes that are unknown. Although Lundsgaard (U.S. Pat. No. 4,997,769) teaches a method for dealing with the residual turbidity that remains after the hemolysis process, it would be advantageous to eliminate hemolysis completely and make spectrophotometric measurements directly in unaltered whole blood.

The Applicants have found that the scattering of light by unaltered (unhemolyzed) whole blood differs in five crucial ways from the turbidity of hemolyzed blood. First, as mentioned previously, the turbidity of hemolyzed blood is insignificant in magnitude in comparison with the light scattering of unhemolyzed whole blood. This conclusion is reinforced by FIG. 2 which shows a measure of light scattering in whole blood before and after hemolysis. For these data, the light scattering in unaltered, whole blood is approximately 20 times greater than after hemolysis. In fact, light scattering by red blood cells in unaltered whole blood is so intense that scattered light predominates over unscattered light after it has passed through as few as 10 layers of red blood cells (C. C. Johnson. J. Assoc. Adv. Med. Instrument. 4:22–27, 1970). Prior art was not designed to accommodate the greater magnitude of the scattering effects of unaltered whole blood.

Second, a fundamental observation is that red blood cells scatter light at relatively large angles (J. M. Steinke and A. P. Shepherd, Applied Optics 27:4027–4033,1988). The Applicants have discovered that, even though most of the light is scattered at small angles, the magnitude of large-angle light scattering is sufficient to cause serious errors in spectrophotometric measurements on whole blood. Prior art does not address the problem of designing practical instruments by capturing the large-angle light scattering of unhemolyzed blood.

Third, the light scattering by red blood cells varies with wavelength in a complicated manner due to physical factors such as the relative size of red blood cells with respect to the wavelength, and the shape of the red blood cells. FIG. 3 shows the wavelength dependence of light scattering by RBCs as predicted by optical theory (R. N. Pittman and B. R. Duling, J. Appl. Physiol. 38:315–320,1975; R. N. Pittman, Ann. Biomed. Eng. 14:119–137, 1986). Prior art does not address the complex wavelength dependence of the scattering effects of unaltered whole blood.

Fourth, as FIG. 4 shows, the light scattering by red blood cells is not only a function of wavelength, but it also depends on the composition of the hemoglobin contained in the red blood cells, i.e. the light scattering depends on the relative concentrations of oxy-, deoxy-, carboxy-, met-, and sulfhemoglobin in the red blood cells. Prior art does not address the complex dependence of light scattering on the concentrations of the individual hemoglobin species in unaltered whole blood.

Fifth, many poorly understood, uncontrolled processes occur in unaltered, whole blood that change its optical properties. Such miscellaneous causes of unpredictable light scattering include 1) the different plasma protein concentrations that determine the refractive index of plasma in one sample versus another, 2) the aggregation of red blood cells in the sample, 3) the different hemoglobin concentrations inside the red blood cells that alter their refractive index, 4) the size and shape of the red blood cells, 5) chylomicrons or other light-scattering lipid particles, 6) cell fragments, 7) microscopic clots, and 8) light-sieving effects of sedimented RBCs.

As shown in the comparative example below, the apparatus of Lundsgaard, U.S. Pat. No. 4,997,769, fails to yield valid results when measuring a sample of unaltered (unhemolyzed) whole blood. Similarly, other prior art that relies on hemolysis such as Brown et al., U.S. Pat. No. 4,134,678; Raffaele, U.S. Pat. No. 4,013,417; and Johansen et al., U.S. Pat. No. 3,972,614 would also fail to yield valid results on unhemolyzed whole blood because these methods also fail to capture the light scattered at large angles by the sample, and because their measurements do not take into account the magnitude, the wavelength dependence, or the hemoglobin-composition-dependence of the light-scattering effects of unaltered whole blood.

SUMMARY OF THE INVENTION

By making spectrophotometric measurements directly on unaltered whole blood and by correcting for the effects of light scattering on the measurements, the present invention eliminates the need to hemolyze the blood sample and the need to chemically convert the various hemoglobin derivatives to a single species. Thus, the present invention overcomes the previously mentioned disadvantages of prior art that employs hemolysis only, hemolysis and dilution, or chemical conversion. By contrast, the present invention makes appropriate measurements of the light scattering by red blood cells and of other light losses in unaltered, whole blood and then uses its assessment of these light losses to correct mathematically the measurements of total hemoglobin concentration and the concentrations of the individual hemoglobin species. By eliminating the need for a hemolyzing apparatus, the present invention avoids the problems caused by hemolysis such as the fragmentation of red and white blood cells into light-scattering particles. Furthermore, the need for pumps, plumbing, and associated control circuitry is eliminated by use of an inexpensive disposable cuvette. Therefore, the problem of clogging of the apparatus is eliminated, and the nondestructive optical test performed by the present invention preserves the blood sample (with its red blood cells intact) for further subsequent analysis.

The present invention includes the following component parts that, employed together and in combination, assess the optical transmittance of a sample of unaltered whole blood to attain an accurate measurement of its total hemoglobin concentration, and the concentrations of the following pigments of interest: bilirubin, oxy-, deoxy-, carboxy-, met-, and sulfhemoglobin:

1. A spectrophotometric apparatus (including an optical cuvette) in which all optical parameters (for example, sample thickness, detector size and shape, sample-to-detector distance, wavelengths, monochromicity, and maximum angle of light capture by detector) are optimal values so as to minimize the contribution of light scattering to the total optical attenuation of unaltered whole blood and so as to maximize the contribution of true optical absorbance.

2. A method for selecting an optimal set of four wavelengths for making the measurements of the concentrations of oxy-, carboxy-, and methemoglobin with the least spectrophotometric error.

3. A set of seven measuring wavelengths, including the four selected by the aforementioned method; wherein the fifth wavelength is chosen specifically from the range of the visible spectrum in which absorption by bilirubin is especially large (475 to 500 nm); wherein the sixth wavelength is chosen specifically from the range of the visible spectrum in which absorption by sulfhemoglobin is especially large (615 to 625 nm); and wherein the seventh wavelength is chosen from that part of the spectrum where absorbance by bilirubin and each of the five hemoglobin species is as small as possible in comparison with the effects of light scattering, and small compared with the absorption by at least one of the pigments of interest at each of the other six wavelengths. The seventh wavelength, the longest wavelength, is preferably shorter than 675 nm to avoid errors due to the possible presence of indocyanine green dye in the sample and longer than 660 nm to avoid the relatively large absorbance of methemoglobin.

4. A second method to correct the aforesaid hemoglobin and bilirubin concentration measurements for the effects of light scattering by red blood cells, by other specific factors, and by nonspecific factors in unaltered whole blood, wherein the errors due to the various light-scattering losses are treated as functions of the wavelength of the measuring radiation and as mathematical functions of the concentrations of oxy-, carboxy-, met-, deoxy-, and sulfhemoglobin present in each analyzed sample.

5. A third method to correct the aforesaid concentration measurements for the effects of finite bandwidth of the substantially monochromatic measuring wavelengths, wherein the errors due to finite bandwidth of the substantially monochromatic measuring wavelengths are treated as functions of the concentrations of oxy-, carboxy-, met-, deoxy-, and sulfhemoglobin present in each analyzed sample.

BRIEF DESCRIPTION OF THE DRAWINGS

FIG. 11a–e includes a graphical computer program listing of an embodiment of the method of FIG. 8.

DETAILED DESCRIPTION

1. Glossary of Terms

1. Specific Scattering Factor: Known factor causing light scattering, and thus light losses, in unaltered whole blood, the predominant example of which is light scattering due to red blood cells (RBCs). Other specific scattering factors include lipid particles, cell fragments, microscopic clots, and light-sieving effects of sedimented RBCs.

2. Nonspecific Scattering Factor: Unknown factor causing light scattering, and thus light losses in unaltered whole blood 3. Total Light-scattering Losses: The sum of light losses due to light scattering by red blood cells, other known causes, and unknown causes. In other words, the sum of light losses due to Specific and Nonspecific scattering Factors.

4.
 a. $HbO_2$=oxyhemoglobin
 b. HbCO=carboxyhemoglobin
 c. Hi=methemoglobin or hemiglobin
 d. Hb=reduced hemoglobin
 e. SHb=sulfhemoglobin
 f. br=bilirubin
 g. Tbr=[br]=total bilirubin concentration 5. Total Hemoglobin Concentration (THb): Sum of the amounts of the various hemoglobin species divided by the volume of blood, i.e., the total amount of hemoglobin in a mixture of oxy-, carboxy-, met-, deoxy-, and sulfhemoglobin divided by the volume of blood. THb=[$HbO_2$]+[HbCO]+[Hi]+[Hb]+[SHb]; THb'=[$HbO_2$]+[HbCO]+[Hi]+[Hb]

6. Hemoglobin Fraction: Amount of a given species (such as oxyhemoglobin) divided by the sum of the amounts of oxy-, carboxy-, met-, deoxy-, and sulfhemoglobin, e.g., fraction of $HbO_2$=0.75

7. Saturation or Relative Concentration: Hemoglobin fraction expressed as a percentage, e.g., $HbO_2$ saturation=75%

8. Apparent Optical Density (OD) or Apparent Absorbance (A): Logarithm of the total attenuation in light intensity, i.e., OD=A=$\log_{10}(I_o/I)$, where $I_o$ is the incident intensity and I is the intensity transmitted through the sample. Note that this is not a re-definition of Beer's Law because the apparent optical density in unaltered whole blood could be due to a combination of true Beer's Law absorbance and light losses due to scattering.

9. Error Index: The sum of the absolute values of the errors that are induced in the measurement of the relative concentration of the given hemoglobin species (either oxy-, carboxy-, or methemoglobin) due to a 1% (relative) change in each of $OD_1, \ldots, OD_4$.

10. Unaltered Whole Blood: Whole blood that has been neither hemolyzed nor diluted.

2. Optical Geometry, other Apparatus, and Mode of Operation

Figure 6:
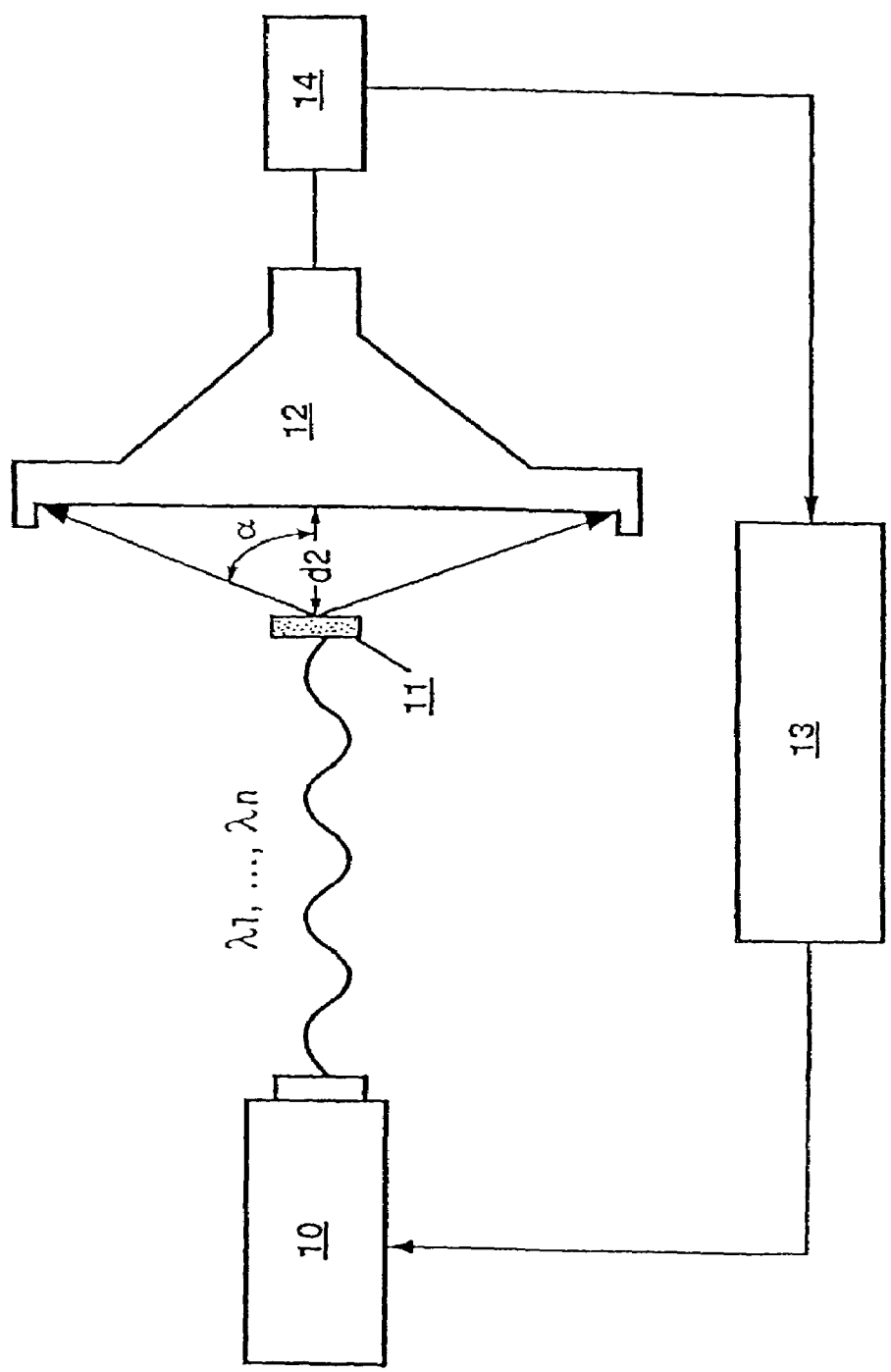
FIG. 6 is a block diagram of the present invention including the optical geometry of the present invention.

FIG. 6 shows the presently preferred embodiment of the present invention which includes a digital computer 13; a computer-controlled light source 10 capable of sequentially emitting at least seven different substantially monochromatic wavelengths; an ultra-thin disposable optical cuvette 11; a large-area light detector 12; and electronic circuitry 14 to amplify the detected signal. In operation, a sample of unaltered (undiluted and unhemolyzed) whole blood is placed in cuvette 11 and irradiated with selected wavelengths of radiation chosen in accordance with the criteria and other principles outlined below. Thus, the normal measurement cycle comprises 1) recording the dark current from the photodetector when the light source 10 is turned off, 2) recording the incident light intensity at each of the selected wavelengths, 3) placing a sample of unaltered (undiluted and unhemolyzed) whole blood in the cuvette 11 and inserting it into the light path, 4) recording the light intensity transmitted through the sample at each of the selected wavelengths, 5) computing the apparent optical densities at each of the selected wavelengths, 6) correcting the concentration measurements for the effects of light scattering by the red blood cells and for nonspecific light-scattering losses, 7) correcting for the effects of the finite spectral bandwidth of the plurality of substantially monochromatic wavelengths, and 8) reporting the final results to the operator. In one embodiment, all measurements are made at a substantially constant temperature.

Following such a measurement cycle, the operator can remove the disposable cuvette from the instrument and discard the sample, or he can withdraw the blood sample from the cuvette and subject the unaltered blood sample to further hematological analyses.

In one embodiment, light source 10 may be a samarium-neon hollow cathode lamp. In another embodiment, light source 10 may be a bank of light-emitting diodes (LED) arranged so that the emissions of each LED pass through a narrow-band optical interference filter before falling on the sample. In yet another embodiment, light source 10 may be a white light source such as a halogen lamp optically coupled to a computer-controlled monochromator. In the first two embodiments, light source 10 may be pulsed at a frequency of approximately 20 Hz in order to achieve a high signal-to-noise ratio by using synchronous detection.

Disposable cuvette 11 has a short optical path chosen to minimize total radiation scattering relative to absorbance by minimizing the number of scattering interactions that a photon is likely to undergo with RBCs. Cuvette 11 may have an optical pathlength of 80 to 150 µm. In one embodiment, the optical pathlength is 90±10 µm.

Large-area radiation detector 12 is sensitive to the selected measuring radiation frequencies and may be placed within a distance d of from 0 to 10 mm, from cuvette 11. Detector 12 has a large active area and is placed close to cuvette 11 in order to capture radiation scattered at wide angles by the whole blood sample contained within cuvette 11. In one embodiment, the distance d from cuvette 11 to detector 12 is no more than 1.0 mm, the active area of detector 12 is at least 150 mm$^2$, and preferably at least 600 mm$^2$, and the receiving half angle α of the detector 12, with respect to the point where the incident radiation impinges on the sample, is at least 30° and preferably at least 70°. This optical design minimizes light losses caused by light scattered at large angles. Detector 12 may be a United Detector Technology detector, PIN-25DP (active area=613 mm$^2$), or may be an SD-1100-11-21-181 detector from Silicon Detector Corporation.

Digital computer 13 may be any type of programmable computer, for example, an Apple MacIntosh computer. In order to render the apparatus as portable as possible, digital computer 13 may be a programmed microprocessor, such as one of the family of Motorola 68000 microprocessors.

Thus, the overall strategy of the optical configuration of the present invention is to maximize the true optical absorbance of unaltered whole blood and to minimize the effects of light scattering so that the apparent optical density of the sample measured by the detector is due primarily to absorbance with as small a contribution by light scattering as possible. However, it should be noted that the optical geometry presented above, when used alone, does not attain commercially acceptable accuracy, i.e. it does not measure the relative hemoglobin concentrations to an accuracy of 1% or less. The optical apparatus of the present invention achieves commercially acceptable accuracy when used in combination with the corrections (described below) that correct the hemoglobin concentration measurements for the effects of light scattering by the red blood cells, for non-specific light-scattering losses, and for the effects of the finite spectral bandwidth of the plurality of substantially monochromatic wavelengths.

3. Choice of Principal Four Wavelengths

In the one embodiment of the present invention, six of the seven measuring wavelengths are chosen as measuring wavelengths for $HbO_2$, HbCO, Hi, Hb, SHb, and bilirubin. Four principal wavelengths among the first six are chosen to measure $HbO_2$, HbCO, Hi and Hb and are chosen to minimize the conversion factors by which errors in the optical density measurements ($OD_1, \ldots, OD_4$) convert to errors in the measurements of % $HbO_2$, % HbCO, and % Hi. The method for selecting these four wavelengths is described as follows.

A fixed hypothetical sample of hemolyzed blood whose hemoglobin composition is 85% $HbO_2$ and 15% Hb, whose total hemoglobin concentration is 16.11 g/dl (10 mmol/L), is considered in a hypothetical cuvette whose pathlength is 100 µm. $OD_1, \ldots, OD_4$ are defined as the absorbances of the hypothetical sample at the four wavelengths $\lambda_1, \ldots, \lambda_4$, thus $$OD_1 = (0.85 \times e_{1HbO2} + 0.15 \times e_{1Hb})/10$$

$$OD_2 = (0.85 \times e_{2HbO2} + 0.15 \times e_{2Hb})/10$$

$$OD_3 = (0.85 \times e_{3HbO2} + 0.15 \times e_{3Hb})/10$$

$$OD_4 = (0.85 \times e_{4HbO2} + 0.15 \times e_{4Hb})/10 \qquad (1)$$

where the extinction coefficients shown are the millimolar extinction coefficients for the two hemoglobin species at the wavelengths $\lambda_1, \ldots, \lambda_4$. Note that once $\lambda_1, \ldots, \lambda_4$, are fixed, % $HbO_2$, % HbCO, % Hi, and % Hb are mathematical functions of $OD_1, \ldots, OD_4$ as shown in the following equations:

$$\begin{bmatrix} OD_1/d \\ OD_2/d \\ OD_3/d \\ OD_4/d \end{bmatrix} = \begin{bmatrix} e_{1HbO2} & e_{1HbCO} & e_{1Hi} & e_{1Hb} \\ e_{2HbO2} & e_{2HbCO} & e_{2Hi} & e_{2Hb} \\ e_{3HbO2} & e_{3HbCO} & e_{3Hi} & e_{3Hb} \\ e_{4HbO2} & e_{4HbCO} & e_{4Hi} & e_{4Hb} \end{bmatrix} \begin{bmatrix} [HbO_2] \\ [HbCO] \\ [Hi] \\ [Hb] \end{bmatrix} \qquad (2)$$

-continued $$\begin{bmatrix} [HbO_2] \\ [HbCO] \\ [Hi] \\ [Hb] \end{bmatrix} = \begin{bmatrix} e_{1HbO2} & e_{1HbCO} & e_{1Hi} & e_{1Hb} \\ e_{2HbO2} & e_{2HbCO} & e_{2Hi} & e_{2Hb} \\ e_{3HbO2} & e_{3HbCO} & e_{3Hi} & e_{3Hb} \\ e_{4HbO2} & e_{4HbCO} & e_{4Hi} & e_{4Hb} \end{bmatrix}^{-1} \begin{bmatrix} OD_1/d \\ OD_2/d \\ OD_3/d \\ OD_4/d \end{bmatrix} \quad (3)$$

$THb' = [HbO_2] + [HbCO] + [Hi] + [Hb];$ $\% HbO_2 = 100 \times [HbO_2]/THb';$ $\% HbCO = 100 \times [HbCO]/THb';$ $\% Hi = 100 \times [Hi]/THb';$ $\% Hb = 100 \times [Hb]/THb';$ Here THb' indicates that SHb is left out of the sum. To account for the effects of light scattering when absorbance is small, Applicants devised the following technique:

Define $OD_1' = (max\{(0.85 \times e_{1HbO2} + 0.15 \times e_{1Hb}), 5\})/10$ $OD_2' = (max\{(0.85 \times e_{2HbO2} + 0.15 \times e_{2Hb}), 5\})/10$ $OD_3' = (max\{(0.85 \times e_{3HbO2} + 0.15 \times e_{3Hb}), 5\})/10$ $OD_4' = (max\{(0.85 \times e_{4HbO2} + 0.15 \times e_{4Hb}), 5\})/10$ (The extinction coefficients are the millimolar absorptivities.) Thus, whenever the millimolar absorptivity falls below 5, then, for the computation of $OD_1'$, it is set equal to 5. Then for each of the three species (oxy-, carboxy-, and methemoglobin), an error index is computed as the sum of the absolute values of the errors that are induced in the measurement of the relative concentration of the given hemoglobin species (either oxy-, carboxy-, or methemoglobin) due to a 1% (relative) change in each of $OD_1', \ldots, OD_4'$. Thus:

Error Index for oxyhemoglobin=$0.01 OD_1' d(\% HbO_2)/d((OD_1)| + 0.01 OD_2' d(\% HbO_2)/d(OD_2)| + 0.01 OD_3' d(\% HbO_2)/d(OD_3)| + 0.01 OD_4' d(\% HbO_2)/d(OD_4)|$.

Error Index for carboxyhemoglobin=$0.01 OD_1' d(\% HbCO)/d(OD_1)| + 0.01 OD_2' d(\% HbCO)/d(OD_2)| + 0.01 OD_3' d(\% HbCO)/d(OD_3)| + 0.01 OD_4' d(\% HbCO)/d(OD_4)|$.

Error Index for methemoglobin=$0.01 OD_1' d(\% Hi)/d(OD_1)| + 0.01 OD_2' d(\% Hi)/d(OD_2)| + 0.01 OD_3' d(\% Hi)/d(OD_3)| + 0.01 OD_4' d(\% Hi)/d(OD_4)|$.

The derivatives, e.g. $d(\% HbCO)/d(OD_3)$, are taken at the fixed values of $OD_1, \ldots, OD_4$ determined for the fixed hypothetical sample whose hemoglobin is comprised of 85% $HbO_2$ and 15% Hb. An error criterion for the quadruple of wavelengths $\lambda_1, \ldots, \lambda_4$ is then defined as the maximum of these three error indices. The mathematical criterion of the present invention consists in selecting the unique quadruple of wavelengths in the 510–630 nm range which minimizes the error criterion. The wavelengths are searched by 2 nm increments. When the extinction coefficient values determined by the inventors are used, the final four wavelengths selected by this criteria are 522, 562, 584 and 600 nm. When the extinction coefficient values of Zwart et al. are used (A. Zwart, E. J. van Kampen and W. G. Zijlstra, Clinical Chemistry 32: 972–978, 1986), the final four wavelengths selected by this criteria are 518, 562, 580, and 590 nm.

Figure 8:
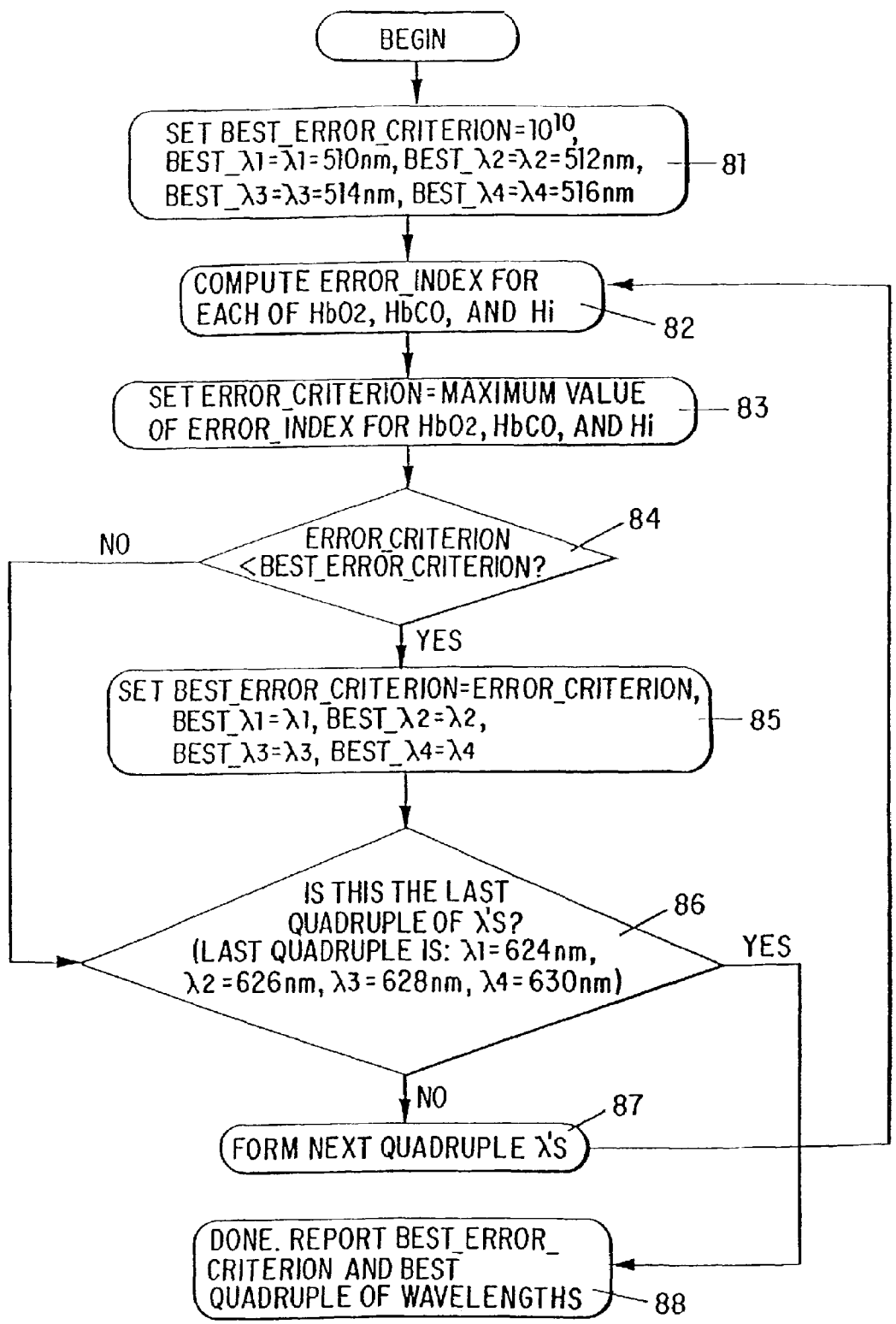
FIG. 8 is a flow chart of the method in accordance with the present invention to select four principal measuring wavelengths.

Referring now to FIG. 8, presented is a flow chart of the method of the present invention to select the unique quadruple of wavelengths, in accordance with the present invention.

Beginning in block 81, the Best Error Criterion is set to $10^{10}$, and the first quadruple of wavelengths is selected. For example, the first quadruple may be 510, 512, 514, and 516 nm. Control then passes to block 82 where the Error Index for each of $HbO_2$, HbCO, and Hi are computed. Then, control passes to block 83 where the Error Criterion is set to the absolute value of the Error Indices calculated in block 82.

Then, in decision block 84, the Error Criterion calculated in block 83 is compared with the Best Error Criterion. If the Error Criterion is less than the Best Error Criterion, control passes to block 85 where the Best Error Criterion is set equal to the Error Criterion and the best quadruple of wavelengths is set equal to the present quadruple of wavelengths. Control then passes to block 86. If, on the other hand, decision block 84 determines that the Error Criterion is not less than the Best Error Criterion, control passes directly to decision block 86.

In decision block 86, it is determined whether the present quadruple of wavelengths is equal to the last quadruple of wavelengths, for example, 624, 626, 628 and 630 nm. If so, control passes to block 88 where the Best Error Criterion and best quadruple of wavelengths is reported. If, on the other hand, block 86 determines that the last quadruple has not been processed, control passes to block 87 where the next quadruple of wavelengths is formed, and control returns to block 82 for continued processing. To form the next quadruple, only one of the wavelengths at a time is changed by 2 nm. This procedure results in the analysis of all possible combinations of four wavelengths between 510 and 630 nm. Any set having duplicate wavelengths is discarded.

FIGS. 11a–e hereto includes a source code listing in LabView graphical language which embodies the method of the flow chart of FIG. 8. In practice, the method of FIG. 8, either in the form of the source code of FIGS. 11a–e, or in an equivalent form, is used to program a computer to perform the wavelength quadruple selecting method of the present invention.

4. Corrections for Light Scattering by RBCs and for Non-specific Light Scattering As defined in the Glossary, a Scattering Factor is any specific or nonspecific cause of light scattering, i.e. any factor, known or unknown, that causes light scattering and hence light losses in unaltered whole blood. Examples are red blood cells, lipid particles, red blood cell aggregation, clotting, sedimentation, etc.

According to the present invention, n measuring wavelengths are employed to measure k constituent components, with n>k, thereby creating an overdetermined system of equations with respect to the chemical compounds being measured. The n–k extra equations provide a means by which errors due to n–k scattering factors can be compensated. Each specific scattering factor in the above definition is assumed to contribute in a well-defined way to the apparent absorbance spectrum of unaltered whole blood placed within cuvette C. For a given scattering factor y, the contribution to the apparent optical density of unaltered whole blood at wavelength i is denoted $OD_{iy}$.

From these considerations, the following equations result:

$$OD_1 = OD_{1abs} + OD_{1yl} + \ldots + OD_{1yp}$$
$$OD_2 = OD_{2abs} + OD_{2yl} + \ldots + OD_{2yp}$$
$$\vdots$$
$$OD_n = OD_{nabs} + OD_{nyl} + \ldots + OD_{nyp}$$

where $1, \ldots, n$ are wavelength indices and $1, \ldots, p$ are scattering factor indices. Since there are k constituent light-absorbing, chemical compounds to be determined, it follows that $n = p + k$. $OD_{iabs}$ is the part of the total optical density due to true optical absorption by the k light-absorbing compounds, i.e., $$OD_{iabs}/d = e_{ix1}c_{x1} + e_{ix2}c_{x2} + \ldots + e_{ixk}c_{xk}$$

where $x_1, \ldots, x_k$ denote the k chemical identities of the light-absorbing compounds to be measured and $c_{x1}, \ldots, c_{xk}$ are their concentrations.

In the context of the present invention, the attenuation of light due to the presence of the scattering factor y is assumed to obey the relationship $$OD_{iy} = s_{iy} m_y d$$

where $s_y = \{s_{1y}, s_{2y}, \ldots, s_{ny}\}$ is the scattering vector associated with the scattering factor y, and $m_y$ is the magnitude of scattering caused by the scattering factor y. Thus it is possible to write the following matrix equation:

$$\begin{bmatrix} OD_1/d \\ OD_2/d \\ \ldots \\ OD_n/d \end{bmatrix} = \begin{bmatrix} e_{1x1} & e_{1x2} & \cdots & e_{1xk} & s_{1y1} & s_{1y2} & \cdots & s_{1yp} \\ e_{2x1} & e_{2x2} & \cdots & e_{2xk} & s_{2y1} & s_{2y2} & \cdots & s_{2yp} \\ & & \cdots & & & & \cdots & \\ e_{nx1} & e_{nx2} & \cdots & e_{nxk} & s_{ny1} & s_{ny2} & \cdots & s_{nyp} \end{bmatrix} \begin{bmatrix} c_{x1} \\ c_{x2} \\ \ldots \\ c_{xk} \\ m_{y1} \\ m_{y2} \\ \ldots \\ m_{yp} \end{bmatrix} \quad (4)$$

The Applicants have discovered that the scattering vectors $s_{yj}$ (where j denotes the scattering factor index) vary with the hemoglobin species present in the sample under test. For example, the scattering vectors $s_{yj}$ are different in completely oxygenated blood and blood completely saturated with carbon monoxide. Therefore, in the present invention, the scattering vectors $s_{yj}$ are described as functions of the concentrations of the hemoglobin species present in the sample under test.

Since each scattering vector $s_{yj}$ depends on the hemoglobin species composition of the sample under test, one further distinguishes such scattering vectors as $s_{yj}(HbO_2)$, $s_{yj}(HbCO)$, etc. For an arbitrary sample of unaltered whole blood, the appropriate vector $s_{yj}$ is computed as $$\begin{bmatrix} s_{1yj} \\ s_{2yj} \\ \ldots \\ s_{nyj} \end{bmatrix} = \begin{bmatrix} s_{1yj}(x_1) & s_{1yj}(x_2) & \cdots & s_{1yj}(x_h) \\ s_{2yj}(x_1) & s_{2yj}(x_2) & \cdots & s_{2yj}(x_h) \\ & \cdots & & \\ s_{nyj}(x_1) & s_{nyj}(x_2) & \cdots & s_{nyj}(x_h) \end{bmatrix} \begin{bmatrix} [x_1]/([x_1]+\ldots+[x_h]) \\ [x_2]/([x_1]+\ldots+[x_h]) \\ \ldots \\ [x_h]/([x_1]+\ldots+[x_h]) \end{bmatrix} \quad (5)$$

Here h is the number of hemoglobin species present among the total number k of light-absorbing compounds, and $x_1, \ldots, x_h$ denote the h hemoglobin species being measured.

According to the present invention, the following scattering factors have been identified: 1) light scattering by red blood cells, a specific scattering factor denoted by the subscript RBC, and 2) a nonspecific scattering factor, denoted by the subscript NS. The nonspecific scattering factor, discovered unexpectedly by the Applicants, significantly increases the utility of the present invention. Data showing the utility of the nonspecific scattering factor over and above the corrections for light scattering by red blood cells are given in FIG. 7 and Table II following the present disclosure of the general method to correct for light scattering.

Disclosed are two embodiments of the corrections for light scattering: Embodiments A and B. In Embodiment A, the following rules hold: only light scattering by the red blood cells is considered (so the nonspecific scattering correction is ignored), and the concentrations of six compounds are measured, namely $HbO_2$, HbCO, Hi, Hb, SHb, and br. In Embodiment B, the following rules hold: both light scattering by red blood cells and nonspecific light scattering are considered, and the concentrations of five compounds are measured, namely $HbO_2$, HbCO, Hi, Hb and br. Both embodiments use the same set of seven wavelengths. As explained above, one wavelength (488 nm) is chosen at which absorbance by bilirubin is relatively large, another wavelength (622 nm) is chosen at which absorbance by sulfhemoglobin is relatively large, and another wavelength (672 nm) is used because light scattering by red blood cells is great in comparison with absorbance by bilirubin and the hemoglobin species. In addition, the mathematical criterion selected an optimal set of four wavelengths (522, 562, 584, and 600 nm) for measuring $HbO_2$, HbCO, Hi with maximum accuracy. If the light source is either a battery of light-emitting diodes combined with optical interference filters or a white light source with a monochromator, these seven wavelengths can be used in either Embodiment A or B of the light-scattering corrections. However, if the samarium-neon hollow-cathode lamp is used, the most appropriate wavelengths among its emission lines are 488.4, 520.1, 562.4, 585.2, 597.5, 621.7, 671.7 nm. Therefore, this set of wavelengths can be used in both Embodiments A and B of the light-scattering corrections.

Once the seven wavelengths have been chosen, values for the extinction coefficients for bilirubin and the hemoglobin species can be determined. Therefore, the following equations obtain in Embodiments A and B of the light-scattering corrections.

EMBODIMENT A $$OD_{iabs}/d = e_{iHbO2}[HbO_2] + e_{iHbCO}[HbCO]e_{iHi}[Hi] + e_{iHb}[Hb] + e_{iSHb}[SHb] + e_{ibr}[br] \quad (6A)$$

$$\begin{bmatrix} OD_1/d \\ OD_2/d \\ OD_3/d \\ OD_4/d \\ OD_5/d \\ OD_6/d \\ OD_7/d \end{bmatrix} = \begin{bmatrix} e_{1HbO_2} & e_{1HbCO} & e_{1Hi} & e_{1Hb} & e_{1SHb} & e_{1br} & s_{1RBC} \\ e_{2HbO_2} & e_{2HbCO} & e_{2Hi} & e_{2Hb} & e_{2SHb} & e_{2br} & s_{2RBC} \\ e_{3HbO_2} & e_{3HbCO} & e_{3Hi} & e_{3Hb} & e_{3SHb} & e_{3br} & s_{3RBC} \\ e_{4HbO_2} & e_{4HbCO} & e_{4Hi} & e_{4Hb} & e_{4SHb} & e_{4br} & s_{4RBC} \\ e_{5HbO_2} & e_{5HbCO} & e_{5Hi} & e_{5Hb} & e_{5SHb} & e_{5br} & s_{5RBC} \\ e_{6HbO_2} & e_{6HbCO} & e_{6Hi} & e_{6Hb} & e_{6SHb} & e_{6br} & s_{6RBC} \\ e_{7HbO_2} & e_{7HbCO} & e_{7Hi} & e_{7Hb} & e_{7SHb} & e_{7br} & s_{7RBC} \end{bmatrix} \begin{bmatrix} [HbO_2] \\ [HbCO] \\ [Hi] \\ [Hb] \\ [SHb] \\ [br] \\ m_{RBCscat} \end{bmatrix}$$

$$THb = [HbO_2] + [HbCO] + [Hi] + [Hb] + [SHb] \quad (7A)$$

$$\begin{bmatrix} s_{1RBC} \\ s_{2RBC} \\ s_{3RBC} \\ s_{4RBC} \\ s_{5RBC} \\ s_{6RBC} \\ s_{7RBC} \end{bmatrix} = \begin{bmatrix} s_{1RBC}(HbO_2) & s_{1RBC}(HbCO) & s_{1RBC}(Hi) & s_{1RBC}(Hb) & s_{1RBC}(SHb) \\ s_{2RBC}(HbO_2) & s_{2RBC}(HbCO) & s_{2RBC}(Hi) & s_{2RBC}(Hb) & s_{2RBC}(SHb) \\ s_{3RBC}(HbO_2) & s_{3RBC}(HbCO) & s_{3RBC}(Hi) & s_{3RBC}(Hb) & s_{3RBC}(SHb) \\ s_{4RBC}(HbO_2) & s_{4RBC}(HbCO) & s_{4RBC}(Hi) & s_{4RBC}(Hb) & s_{4RBC}(SHb) \\ s_{5RBC}(HbO_2) & s_{5RBC}(HbCO) & s_{5RBC}(Hi) & s_{5RBC}(Hb) & s_{5RBC}(SHb) \\ s_{6RBC}(HbO_2) & s_{6RBC}(HbCO) & s_{6RBC}(Hi) & s_{6RBC}(Hb) & s_{6RBC}(SHb) \\ s_{7RBC}(HbO_2) & s_{7RBC}(HbCO) & s_{7RBC}(Hi) & s_{7RBC}(Hb) & s_{7RBC}(SHb) \end{bmatrix} \begin{bmatrix} [HbO_2]/THb \\ [HbCO]/THb \\ [Hi]/THb \\ [Hb]/THb \\ [SHb]/THb \end{bmatrix}$$

EMBODIMENT B $$OD_{iabs}/d = e_{iHbO2}[HbO_2] + e_{iHbCO}[HbCO]e_{iHi}[Hi] + e_{iHb}[Hb] + e_{ibr}[br] \quad (6B)$$

$$\begin{bmatrix} OD_1/d \\ OD_2/d \\ OD_3/d \\ OD_4/d \\ OD_5/d \\ OD_6/d \\ OD_7/d \end{bmatrix} = \begin{bmatrix} e_{1HbO2} & e_{1HbCO} & e_{1Hi} & e_{1Hb} & e_{1br} & s_{1RBC} & s_{1NS} \\ e_{2HbO2} & e_{2HbCO} & e_{2Hi} & e_{2Hb} & e_{2br} & s_{2RBC} & s_{2NS} \\ e_{3HbO2} & e_{3HbCO} & e_{3Hi} & e_{3Hb} & e_{3br} & s_{3RBC} & s_{3NS} \\ e_{4HbO2} & e_{4HbCO} & e_{4Hi} & e_{4Hb} & e_{4br} & s_{4RBC} & s_{4NS} \\ e_{5HbO2} & e_{5HbCO} & e_{5Hi} & e_{5Hb} & e_{5br} & s_{5RBC} & s_{5NS} \\ e_{6HbO2} & e_{6HbCO} & e_{6Hi} & e_{6Hb} & e_{6br} & e_{6RBC} & e_{6NS} \\ e_{7HbO2} & e_{7HbCO} & e_{7Hi} & e_{7Hb} & e_{7br} & s_{7RBC} & s_{7NS} \end{bmatrix} \begin{bmatrix} [HbO_2] \\ [HbCO] \\ [Hi] \\ [Hb] \\ [br] \\ m_{RBCscat} \\ m_{NSscat} \end{bmatrix}$$

$$THb' = [HbO_2] + [HbCO] + [Hi] + [Hb] + [SHb] \quad (7B)$$

$$\begin{bmatrix} s_{1RBC} \\ s_{2RBC} \\ s_{3RBC} \\ s_{4RBC} \\ s_{5RBC} \\ s_{6RBC} \\ s_{7RBC} \end{bmatrix} = \begin{bmatrix} s_{1RBC}(HbO_2) & s_{1RBC}(HbCO) & s_{1RBC}(Hi) & s_{1RBC}(Hb) \\ s_{2RBC}(HbO_2) & s_{2RBC}(HbCO) & s_{2RBC}(Hi) & s_{2RBC}(Hb) \\ s_{3RBC}(HbO_2) & s_{3RBC}(HbCO) & s_{3RBC}(Hi) & s_{3RBC}(Hb) \\ s_{4RBC}(HbO_2) & s_{4RBC}(HbCO) & s_{4RBC}(Hi) & s_{4RBC}(Hb) \\ s_{5RBC}(HbO_2) & s_{5RBC}(HbCO) & s_{5RBC}(Hi) & s_{5RBC}(Hb) \\ s_{6RBC}(HbO_2) & s_{6RBC}(HbCO) & s_{6RBC}(Hi) & s_{6RBC}(Hb) \\ s_{7RBC}(HbO_2) & s_{7RBC}(HbCO) & s_{7RBC}(Hi) & s_{7RBC}(Hb) \end{bmatrix} \begin{bmatrix} [HbO_2]/THb' \\ [HbCO]/THb' \\ [Hi]/THb' \\ [Hb]/THb' \end{bmatrix}$$

$$\begin{bmatrix} s_{1NS} \\ s_{2NS} \\ s_{3NS} \\ s_{4NS} \\ s_{5NS} \\ s_{6NS} \\ s_{7NS} \end{bmatrix} = \begin{bmatrix} s_{1NS}(HbO_2) & s_{1NS}(HbCO) & s_{1NS}(Hi) & s_{1NS}(Hb) \\ s_{2NS}(HbO_2) & s_{2NS}(HbCO) & s_{2NS}(Hi) & s_{2NS}(Hb) \\ s_{3NS}(HbO_2) & s_{3NS}(HbCO) & s_{3NS}(Hi) & s_{3NS}(Hb) \\ s_{4NS}(HbO_2) & s_{4NS}(HbCO) & s_{4NS}(Hi) & s_{4NS}(Hb) \\ s_{5NS}(HbO_2) & s_{5NS}(HbCO) & s_{5NS}(Hi) & s_{5NS}(Hb) \\ s_{6NS}(HbO_2) & s_{6NS}(HbCO) & s_{6NS}(Hi) & s_{6NS}(Hb) \\ s_{7NS}(HbO_2) & s_{7NS}(HbCO) & s_{7NS}(Hi) & s_{7NS}(Hb) \end{bmatrix} \begin{bmatrix} [HbO_2]/THb' \\ [HbCO]/THb' \\ [Hi]/THb' \\ [Hb]/THb' \end{bmatrix} \quad (8B)$$

wherein [HbO$_2$], [HbCO], [Hi], [Hb], and [SHb] are the concentrations of the indicated hemoglobin species in the sample, $m_{RBCscat}$ and $m_{NSscat}$ are magnitudes of light scattering by the red blood cells and by the nonspecific factor, THb=[HbO$_2$]+[HbCO]+[Hi]+[Hb]+[SHb], and THb'= [HbO$_2$]+[HbCO]+[Hi]+[Hb]. OD$_1$, . . . , OD$_7$ are the apparent optical densities of a sample of unaltered whole blood measured at each of the seven wavelengths, 488.4, 520.1, 562.4, 585.2, 597.5, 621.7, 671.7 nm, respectively. The method of finding the correct values for the scattering vectors $S_{RBC}$ and $S_{NS}$ when the relative concentrations (e.g., [HbO2]/THb) are initially unknown proceeds as follows. Default values for the scattering vectors $S_{RBC}$ and $S_{NS}$ are chosen to be the scattering vectors $S_{RBC}$(HbO$_2$) and $S_{NS}$(HbO$_2$), i.e. those values that are valid in case the sample is comprised purely of oxyhemoglobin.

With the vectors $S_{RBC}$(HbO$_2$) and $S_{NS}$(HbO$_2$) placed into the matrix equation 6A or 6B above, initial values for [HbO2], [HbCO], [Hi], [Hb], [br], $m_{RBCscat}$ [SHb] (Embodiment A) or $m_{NSscat}$ (Embodiment B) are computed. The initial hemoglobin and bilirubin concentrations are not yet accurate enough to report as final results, but they are sufficiently close to the true values to compute more accurate $S_{RBC}$ and $S_{NS}$ vectors for the given blood sample according to equation 7A or equations 7B and 8B. With the newly computed $S_{RBC}$ vector (Embodiment A), or the both the new $S_{RBC}$ and $S_{NS}$ vectors (Embodiment B) placed into the matrix equation 6A or 6B above, the quantities [HbO$_2$], [HbCO], [Hi], [Hb], [br], $m_{RBCscat}$, and [SHb] or $m_{NSscat}$ are recomputed. These quantities are more accurate than their initial values because the $S_{RBC}$ or both $S_{RBC}$ and $S_{NS}$ vectors used in obtaining them are more accurate than those used in the initial estimates. This procedure of using the most recently computed hemoglobin concentrations to compute more accurate $S_{RBC}$ or both $S_{RBC}$ and $S_{NS}$ vectors and in turn using the most recently computed $S_{RBC}$ or both $S_{RBC}$ and $S_{NS}$ vectors to compute more accurate hemoglobin and bilirubin concentrations provides an iterative scheme whereby the hemoglobin and bilirubin concentrations quickly converge to their final values. In both embodiments A and B, the fourth iteration of the computation of these concentrations is sufficiently accurate to report.

Figure 1:
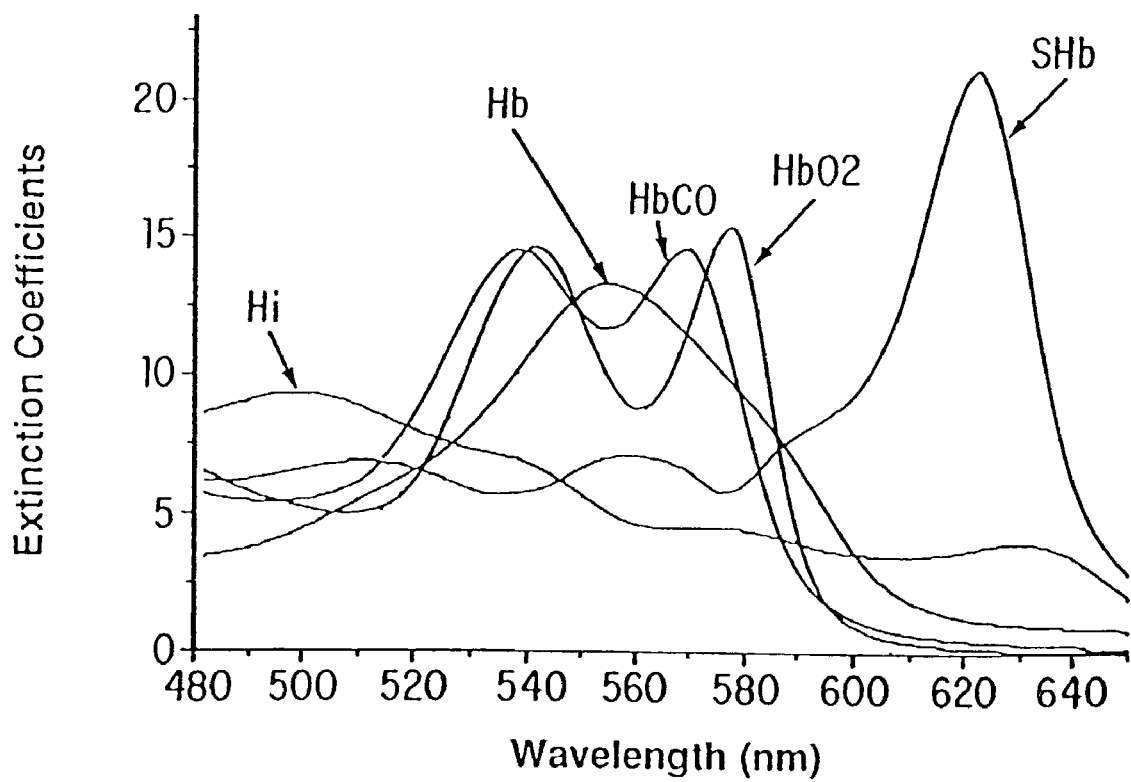
FIG. 1 is a graph of absorbance spectra for the five primary hemoglobin species.
Figure 2:
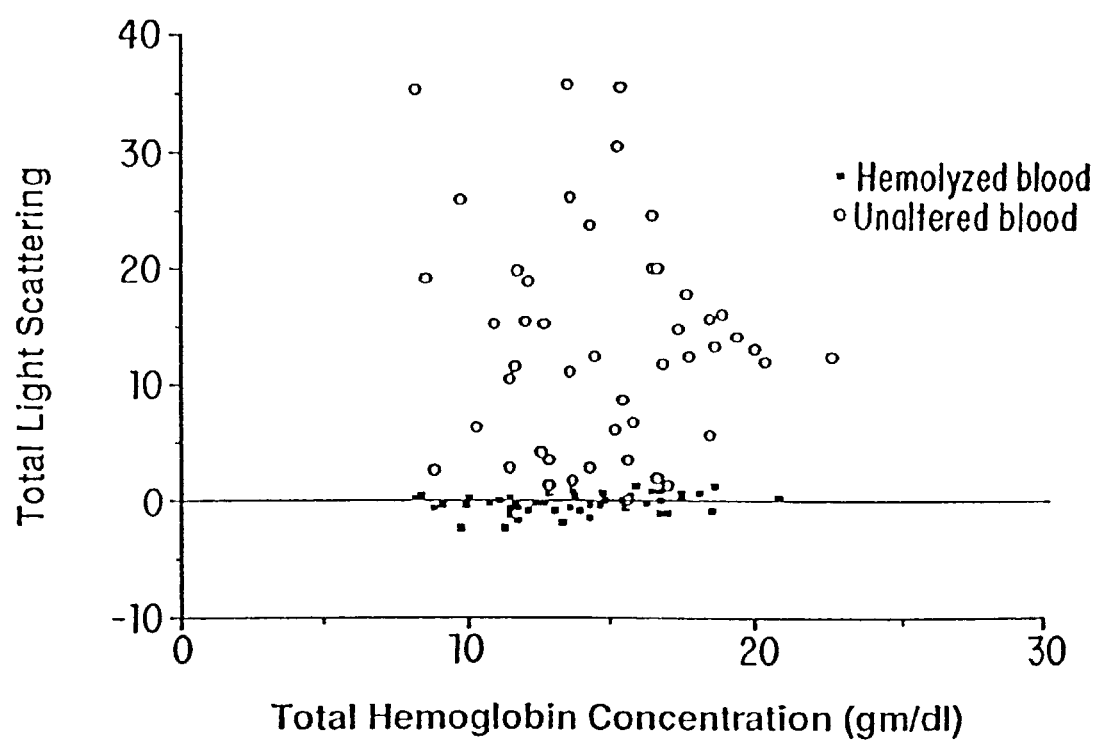
FIG. 2 is a graph comparing the light scattering of unaltered whole blood with that of hemolyzed blood.
Figure 3:
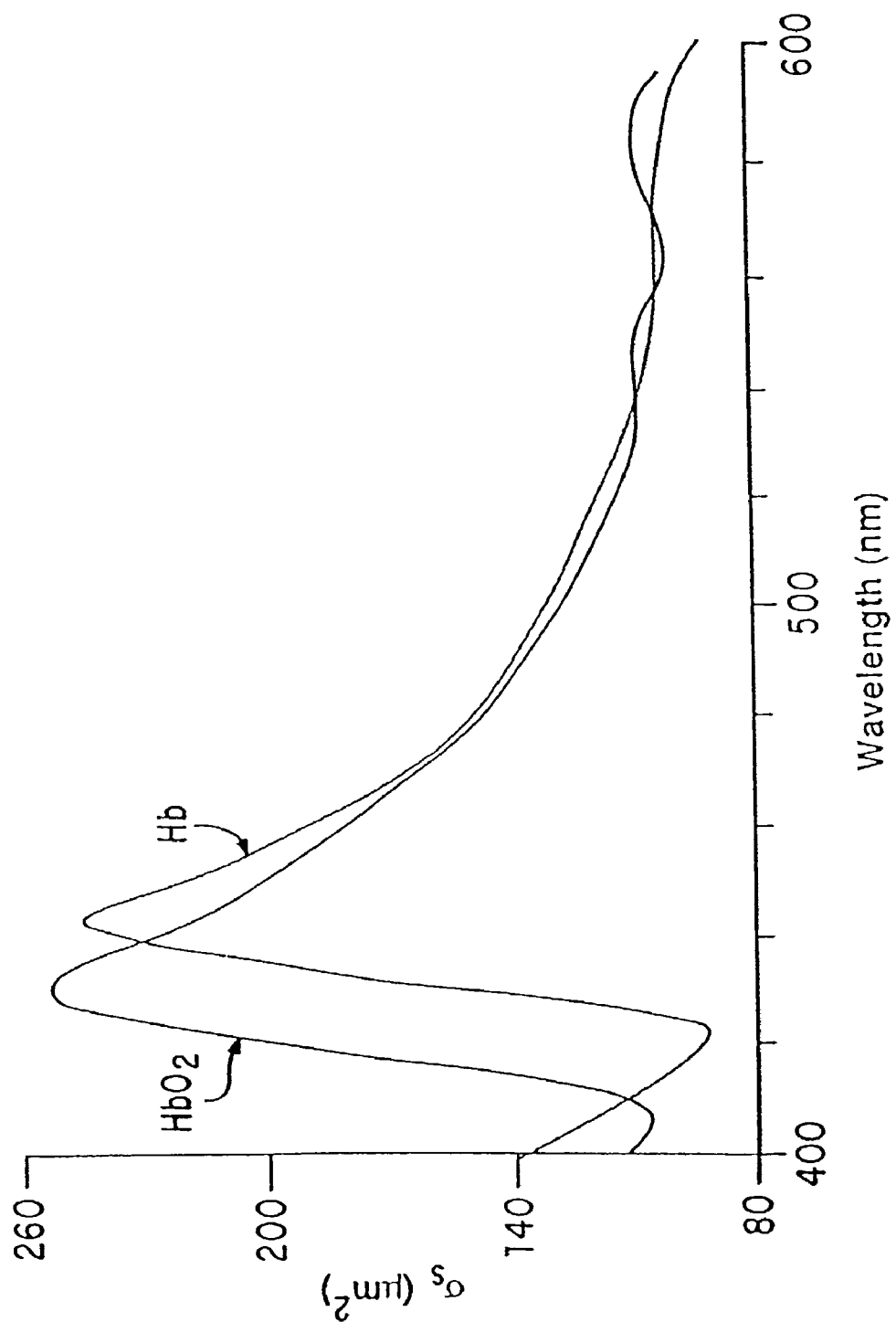
FIG. 3 is a graph of the theoretical wavelength dependence of the scattering of light by red blood cells.
Figure 4:
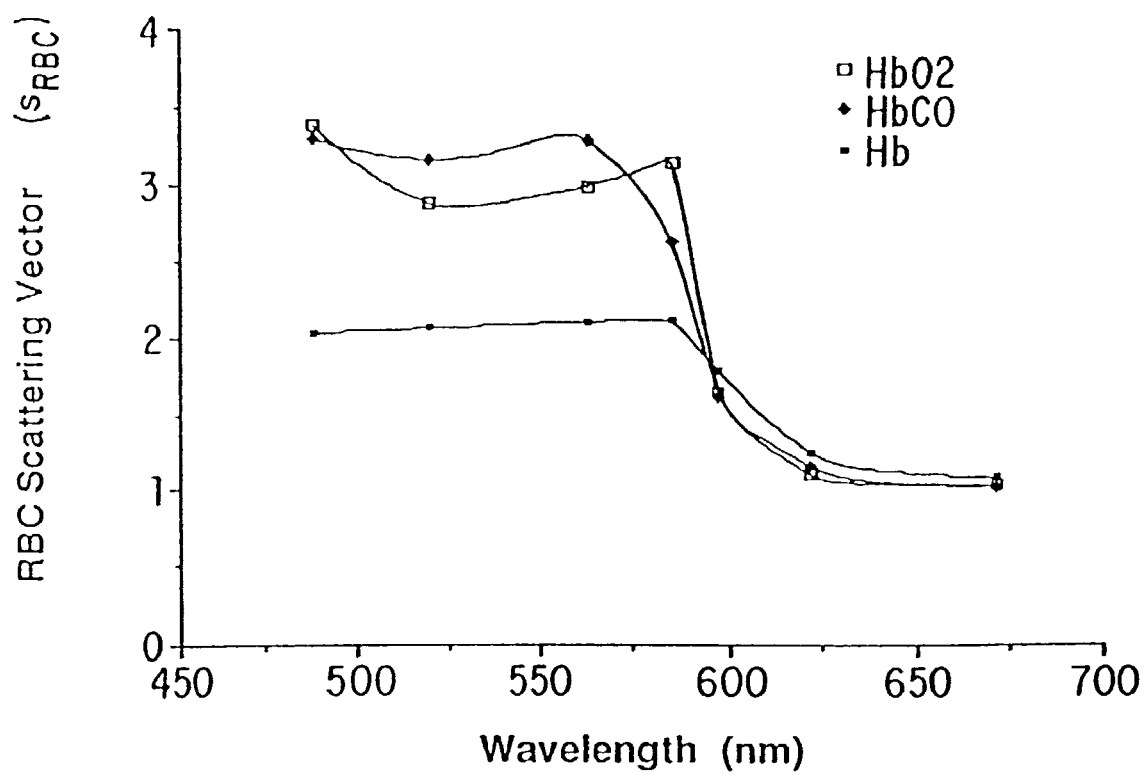
FIG. 4 is a graph of the wavelength dependence of the light scattering by red blood cells in unaltered whole blood in the present invention for varying hemoglobin compositions of whole blood.
Figure 5:
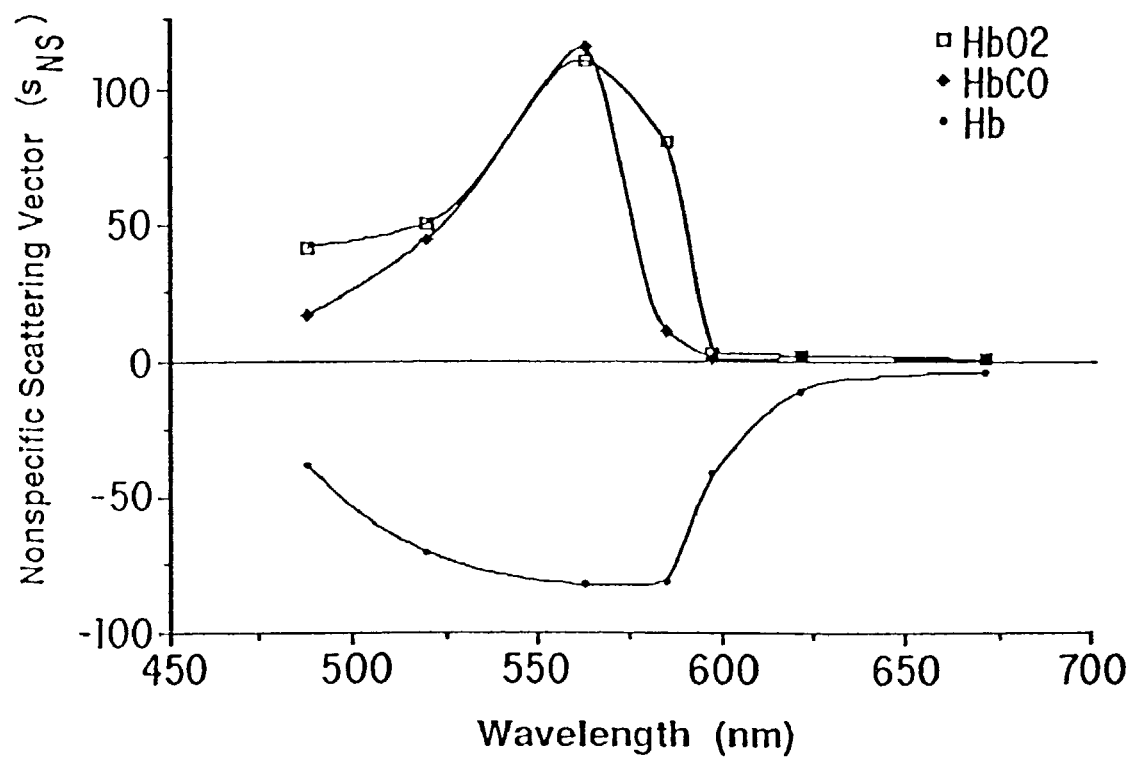
FIG. 5 is a graph of the wavelength dependence of the nonspecific light-scattering losses in unaltered whole blood for varying hemoglobin compositions of whole blood.

Table I shows the values for the scattering vectors $S_{RBC}$(HbO$_2$), $S_{NS}$(HbO$_2$), $S_{RBC}$(HbCO), $S_{NS}$(HbCO), $S_{RBC}$(Hb), and $S_{NS}$(Hb), which the Applicants have measured and have found to be valid for both present Embodiments A and B of the light-scattering corrections. FIGS. 4 and 5 show the same data graphically at each of the measuring wavelengths (488.4, 520.1, 562.4, 585.2, 597.5, 621.7, and 671.7 nm). The present embodiment of the invention does not include measured values for the scattering vectors $S_{RBC}$(Hi), $S_{NS}$(Hi) or $S_{RBC}$(SHb) because these less common hemoglobin species usually occur in low concentrations and because the most common hemoglobin species HbO$_2$, HbCO, and Hb usually dominate the blood composition in healthy and diseased patients. However, in Table I are given default values for the vectors $S_{RBC}$(Hi), $S_{NS}$(Hi) and $S_{RBC}$(SHb). Moreover, the equations are general, so it is within the scope of the present invention to include measured values for these scattering vectors as well.

Table I. Scattering Vectors for Various Hemoglobin Species In this table the indices 1, . . . , 7 refer to the seven wavelengths 488.4, 520.1, 562.4, 585.2, 597.5, 621.7, and 671.7 nm, respectively.

a. Scattering Vectors for HbO$_2$:

| | |
|---|---|
| $S_{1NS}$(HbO$_2$) | 41.33 |
| $S_{2NS}$(HbO$_2$) | 50.00 |
| $S_{3NS}$(HbO$_2$) | 109.37 |
| $S_{4NS}$(HbO$_2$) | 80.45 |
| $S_{5NS}$(HbO$_2$) | 3.18 |
| $S_{6NS}$(HbO$_2$) | 2.00 |
| $S_{7NS}$(HbO$_2$) | 0.81 |
| $S_{1RBC}$(HbO$_2$) | 3.375 |
| $S_{2RBC}$(HbO$_2$) | 2.869 |
| $S_{3RBC}$(HbO$_2$) | 2.977 |
| $S_{4RBC}$(HbO$_2$) | 3.133 |
| $S_{5RBC}$(HbO$_2$) | 1.647 |
| $S_{6RBC}$(HbO$_2$) | 1.109 |
| $S_{7RBC}$(HbO$_2$) | 1.036 | b. Scattering Vectors for HbCO:

| | |
|---|---|
| $S_{1NS}$(HbCO) | 16.46 |
| $S_{2NS}$(HbCO) | 44.27 |
| $S_{3NS}$(HbCO) | 114.30 |
| $S_{4NS}$(HbCO) | 10.47 |
| $S_{5NS}$(HbCO) | 0.90 |
| $S_{6NS}$(HbCO) | 1.32 |
| $S_{7NS}$(HbCO) | 1.10 |
| $S_{1RBC}$(HbCO) | 3.288 |
| $S_{2RBC}$(HbCO) | 3.152 |
| $S_{3RBC}$(HbCO) | 3.274 |
| $S_{4RBC}$(HbCO) | 2.619 |
| $S_{5RBC}$(HbCO) | 1.618 |
| $S_{6RBC}$(HbCO) | 1.168 |
| $S_{7RBC}$(HbCO) | 1.024 | c. Scattering Vectors for Hi:

| | |
|---|---|
| $S_{1NS}$(Hi) | 6.216 |
| $S_{2NS}$(Hi) | 6.629 |
| $S_{3NS}$(Hi) | 7.065 |
| $S_{4NS}$(Hi) | 7.200 |
| $S_{5NS}$(Hi) | 8.944 |
| $S_{6NS}$(Hi) | 21.220 |
| $S_{7NS}$(Hi) | 2.800 |
| $S_{1RBC}$(Hi) | 1.000 |
| $S_{2RBC}$(Hi) | 1.000 |
| $S_{3RBC}$(Hi) | 1.000 |
| $S_{4RBC}$(Hi) | 1.000 |
| $S_{5RBC}$(Hi) | 1.000 |
| $S_{6RBC}$(Hi) | 1.000 |
| $S_{7RBC}$(Hi) | 1.000 | d. Scattering Vectors for Hb:

| | |
|---|---|
| $S_{1NS}$(Hb) | −38.13 |
| $S_{2NS}$(Hb) | −70.24 |
| $S_{3NS}$(Hb) | −82.10 |
| $S_{4NS}$(Hb) | −81.07 |
| $S_{5NS}$(Hb) | −41.43 |
| $S_{6NS}$(Hb) | −10.81 |
| $S_{7NS}$(Hb) | −4.03 |
| $S_{1RBC}$(Hb) | 2.037 |
| $S_{2RBC}$(Hb) | 2.063 |
| $S_{3RBC}$(Hb) | 2.108 |
| $S_{4RBC}$(Hb) | 2.130 |
| $S_{5RBC}$(Hb) | 1.785 |
| $S_{6RBC}$(Hb) | 1.259 |
| $S_{7RBC}$(Hb) | 1.092 | e. Scattering Vector for SHb:

| | |
|---|---|
| $S_{1RBC}(SHb)$ | 1.000 |
| $S_{2RBC}(SHb)$ | 1.000 |
| $S_{3RBC}(SHb)$ | 1.000 |
| $S_{4RBC}(SHb)$ | 1.000 |
| $S_{5RBC}(SHb)$ | 1.000 |
| $S_{6RBC}(SHb)$ | 1.000 |
| $S_{7RBC}(SHb)$ | 1.000 |

Figure 7:
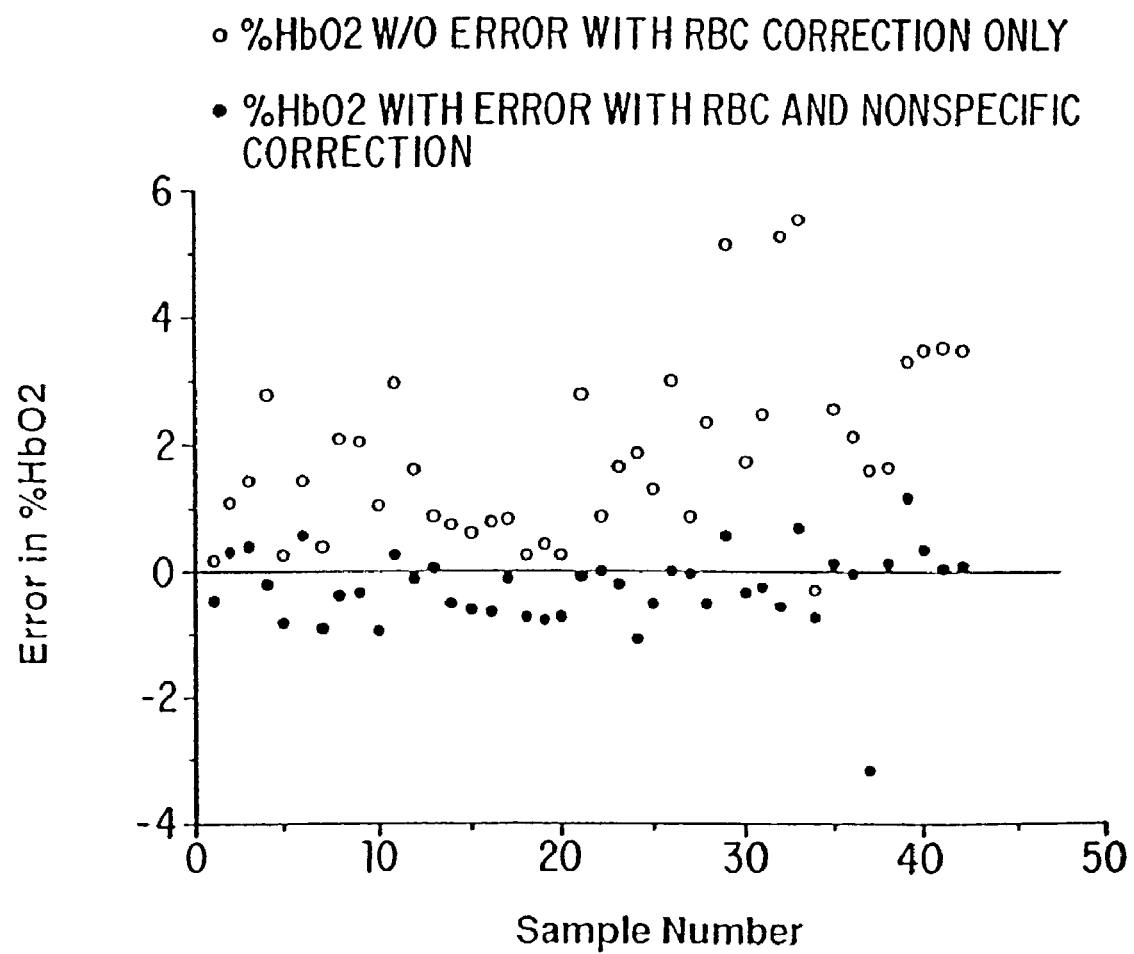
FIG. 7 is a graph of the errors in the measurements of relative oxyhemoglobin concentration with and without the corrections for nonspecific light scattering.

The nonspecific scattering factor (NS) discovered by the Applicants provides a refinement of the more coarse correction for scattering by the red blood cells (RBC). Table II and FIG. 7 show that the nonspecific scattering correction improves the method over and above the accuracy achieved by the RBC correction alone. Table II contains the errors in the measurement of unaltered whole blood fully saturated with carbon monoxide with and without the nonspecific scattering correction.

TABLE II

Efficacy of the Corrections for Nonspecific Light scattering.

| Standard Deviation of Error | % $HbO_2$ | % HbCO | % Hi | % Hb |
|---|---|---|---|---|
| RBC correction only | 1.41 | 3.19 | 2.25 | 0.50 |
| RBC & nonspecific correction | 0.67 | 1.28 | 0.88 | 0.53 |

5. Corrections for the Effect of the Finite Spectral Bandwidth of the Light Source According to the present invention, a method is used to correct the measurements of the concentrations of $HbO_2$, HbCO, Hi, Hb, SHb, and br for the effects of the finite bandwidth of the substantially monochromatic measuring wavelengths. This method is not necessary when the measuring wavelengths provided by light source B are sufficiently monochromatic, as is the case when the substantially monochromatic wavelengths are provided by isolated emission lines of a hollow cathode lamp. However, if the half-intensity bandwidths of the measuring wavelengths are greater than 1.0 nm, as they would be for a battery of LEDs and optical interference filters, this method proves beneficial.

The corrections for the finite spectral width of the light source are necessary because the molar extinction coefficients of the hemoglobin species vary rapidly with wavelength. Thus, when a given spectral width of substantially monochromatic light is used, a range of (wavelength-dependent) extinction coefficients is represented. For fixed spectral bandwidths of the substantially monochromatic wavelengths provided by light source B and over the range of ODs encountered in operation of the apparatus of the present invention, the extinction coefficients of the hemoglobin species are linear functions of the concentrations of HbO2, HbCO, Hi, Hb, SHb, and bilirubin present in the sample under test, and the corrections in concentrations (given below) are linear functions of $[HbO_2]$, [HbCO], [Hi], [Hb], [SHb], and Tbr.

When corrections for the finite spectral bandwidth of the light source are necessary, the order of operation of the invention should be first to measure the optical densities at each of the seven wavelengths, then to apply the corrections for light scattering by the red blood cells and for nonspecific light scattering losses, and finally to make the corrections for the finite spectral bandwidth of the light source.

The method for the compensation of errors due the effects of the finite bandwidths of the substantially monochromatic wavelengths emitted by light source B proceeds as follows. After values for the concentrations have been corrected for the effects of light scattering by the red blood cells and for nonspecific light-scattering losses, the corrected concentration values, [HbO2], [HbCO], [Hi], [Hb], [SHb], and Tbr, are then used to compute spectral bandwidth corrections according to the following matrix equations:

$$\begin{bmatrix} [HbO_2]_{correction} \\ [HbCO]_{correction} \\ [Hi]_{correction} \\ [Hb]_{correction} \\ [SHb]_{correction} \\ [br]_{correction} \end{bmatrix} = \begin{bmatrix} a_{O2,O2} & a_{O2,CO} & a_{O2,Hi} & a_{O2,Hb} & a_{O2,SHb} & a_{O2,br} \\ a_{CO,O2} & a_{CO,CO} & a_{CO,Hi} & a_{CO,Hb} & a_{CO,SHb} & a_{CO,br} \\ a_{Hi,O2} & a_{Hi,CO} & a_{Hi,Hi} & a_{Hi,Hb} & a_{Hi,SHb} & a_{Hi,br} \\ a_{Hb,O2} & a_{Hb,CO} & a_{Hb,Hi} & a_{Hb,Hb} & a_{Hb,SHb} & a_{Hb,br} \\ a_{SHb,O2} & a_{SHB,CO} & a_{SHb,Hi} & a_{SHb,Hb} & a_{SHb,SHb} & a_{SHb,br} \\ a_{br,O2} & a_{br,CO} & a_{br,Hi} & a_{br,Hb} & a_{br,SHb} & a_{br,br} \end{bmatrix} \begin{bmatrix} [HbO_2] \\ [HbCO] \\ [Hi] \\ [Hb] \\ [SHb] \\ [br] \end{bmatrix} \quad (9A)$$

$$\begin{bmatrix} [HbO_2]_{correction} \\ [HbCO]_{correction} \\ [Hi]_{correction} \\ [Hb]_{correction} \\ [br]_{correction} \end{bmatrix} = \begin{bmatrix} a_{O2,O2} & a_{O2,CO} & a_{O2,Hi} & a_{O2,Hb} & a_{O2,br} \\ a_{CO,O2} & a_{CO,CO} & a_{CO,Hi} & a_{CO,Hb} & a_{CO,br} \\ a_{Hi,O2} & a_{Hi,CO} & a_{Hi,Hi} & a_{Hi,Hb} & a_{Hi,br} \\ a_{Hb,O2} & a_{Hb,CO} & a_{Hb,Hi} & a_{Hb,Hb} & a_{Hb,br} \\ a_{br,O2} & a_{br,CO} & a_{br,Hi} & a_{br,Hb} & a_{br,br} \end{bmatrix} \begin{bmatrix} [HbO_2] \\ [HbCO] \\ [Hi] \\ [Hb] \\ [br] \end{bmatrix} \quad (9B)$$

The final concentrations are then computed according to the following formulae:

$$[HbO_2]_{final} = [HbO_2] + [HbO_2]_{correction}$$

$$[HbCO]_{final} = [HbCO] + [HbCO]_{correction}$$

$$[Hi]_{final} = [Hi] + [Hi]_{correction}$$

$$[Hb]_{final} = [Hb] + [Hb]_{correction}$$

$$[SHb]_{final} = [SHb] + [SHb]_{correction}$$

$$[br]_{final} = [br] + [br]_{correction}$$

These matrix equations are completely general in that the measurement error that is due to the effects of finite bandwidth can depend on the hemoglobin composition of the sample under test. When this method is used, the extinction coefficients in matrices 6A and 6B must be the extrapolated values for the limit of small concentrations. The matrices in equations 9A and 9B depend on the values of the particular measuring wavelengths and on the individual bandwidths and spectral distributions of the light at each of these wavelengths.

Figure 9:
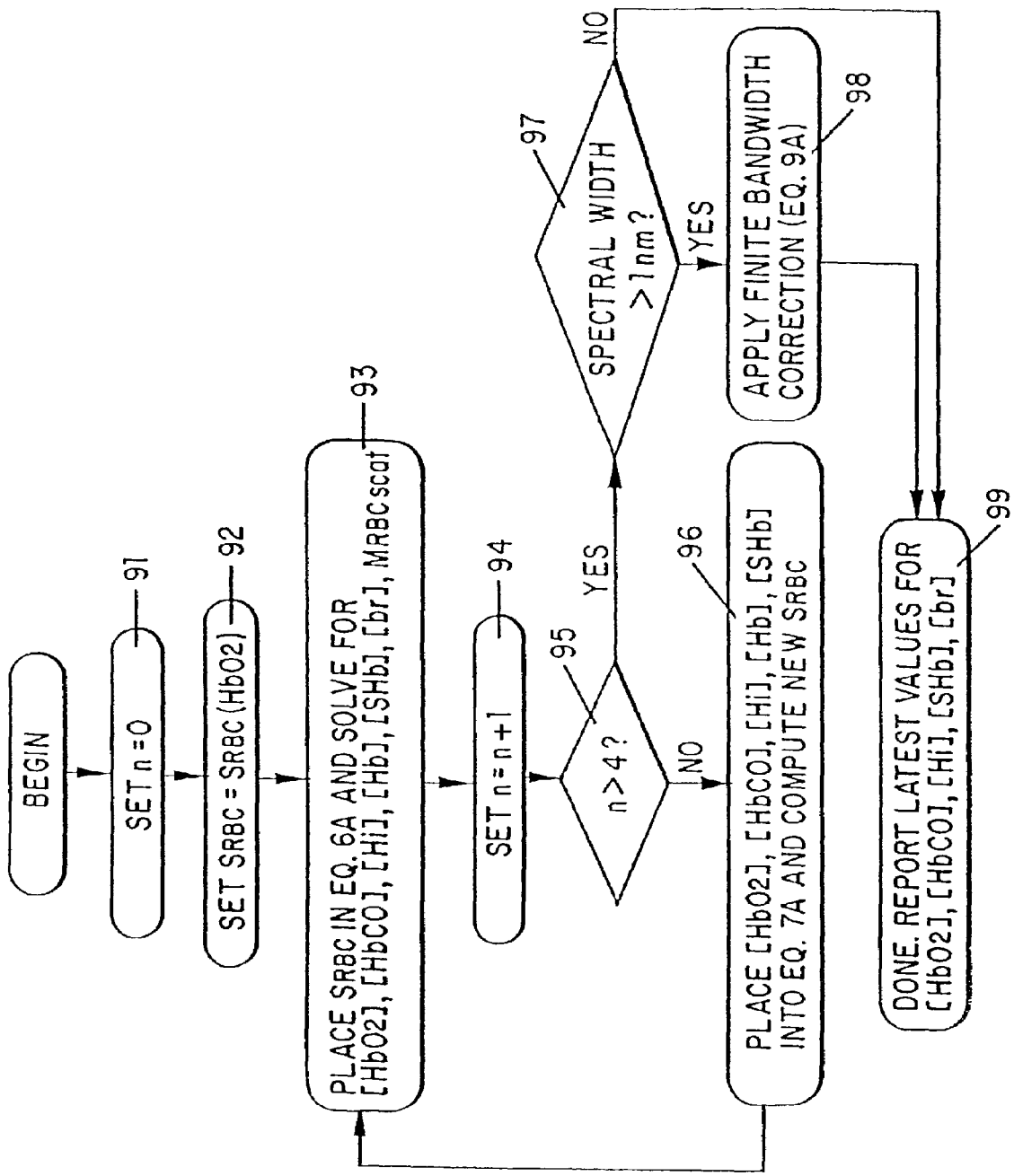
FIG. 9 is a flow chart of a first method of operating the apparatus of FIG. 6, in accordance with the present invention, to correct for light scattering.

Referring now to FIG. 9, presented is a flow chart of the method of operating the apparatus of FIG. 6 to perform the method of Embodiment A, to correct for light scattering in accordance with the present invention.

Beginning in block 91, the counter n is initialized to zero. Then, in block 92, scattering vector $S_{RBC}$ is set equal to $S_{RBC}$ (HbO$_2$). Then, in block 93 equation 6A is used to solve for [HbO$_2$], [HbCO], [Hi], [Hb], [SHb], [br], and $m_{RBCscat}$.

Then, control passes to block 94 where the counter n is incremented by one. In block 95, it is determined whether the counter n is greater than four. If not, control passes to block 96 where the quantities calculated for the concentrations in step 93 are inserted into equation 7A to compute a new value for $S_{RBC}$. Control then returns to block 93. If, on the other hand, decision block 95 determines that counter n is greater than four, control passes to decision block 97 where it is determined whether the spectral width is greater than 1 nm. If so, control passes to block 98 where the finite bandwidth correction of equation 9A is performed. Then, in block 99, the latest values for the concentrations of the six constituent components are reported. If, on the other hand, decision block 97 determines that the spectral width is not greater than 1 nm, control passes directly to block 99 for report of the concentrations.

Appendix A includes a source code listing in the C programming language which embodies the method of the flow chart of FIG. 9. In practice, the method of the flow chart of FIG. 9 embodied in the source code program of Appendix A or an equivalent program, is used to program computer 13 of FIG. 6, to cause the apparatus of FIG. 6 to perform the method of Embodiment A to correct for light scattering.

Figure 10:
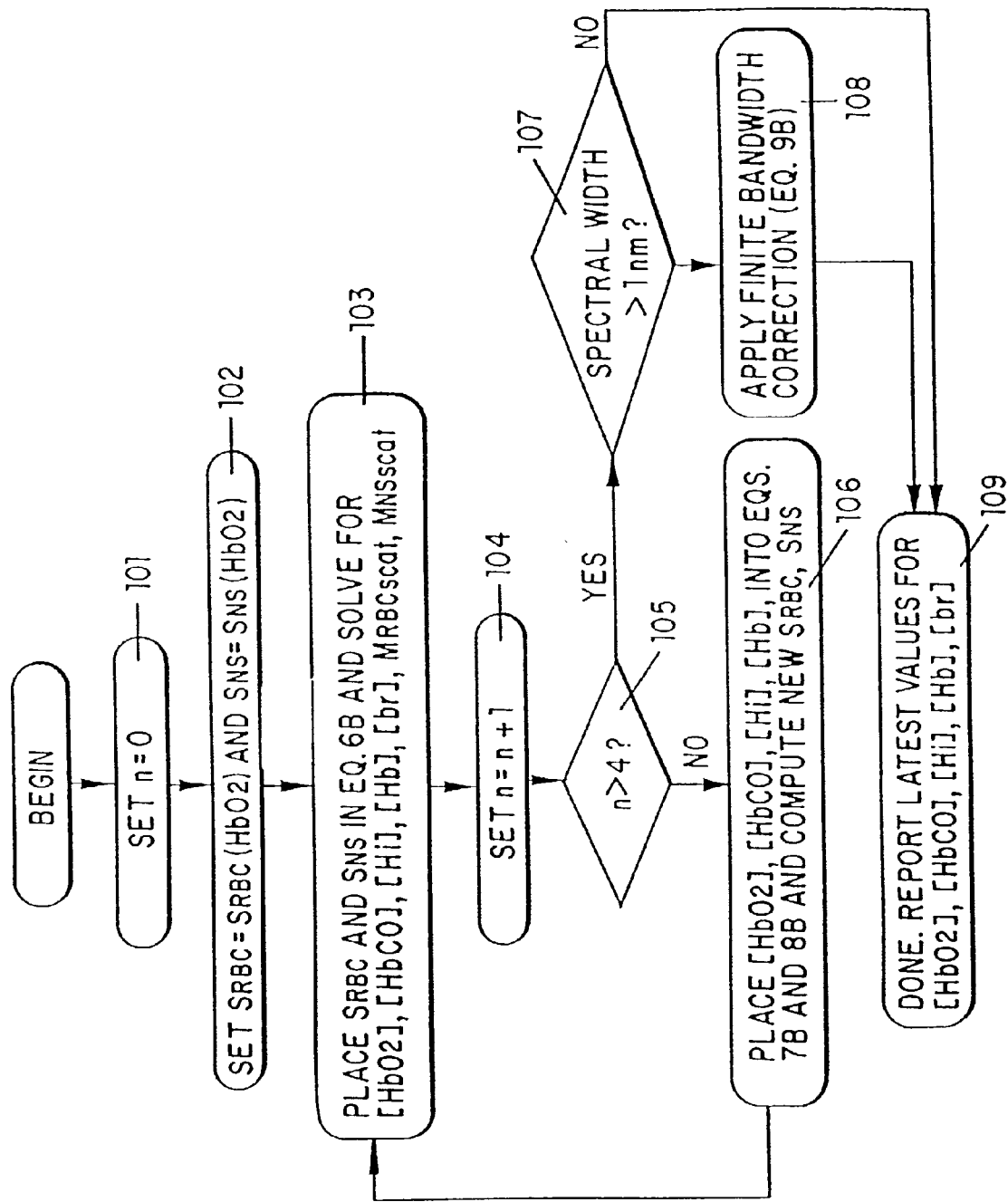
FIG. 10 is a flow chart of a second method of operating the apparatus of FIG. 6, in accordance with the present invention, to correct for light scattering.
Figure 11A:
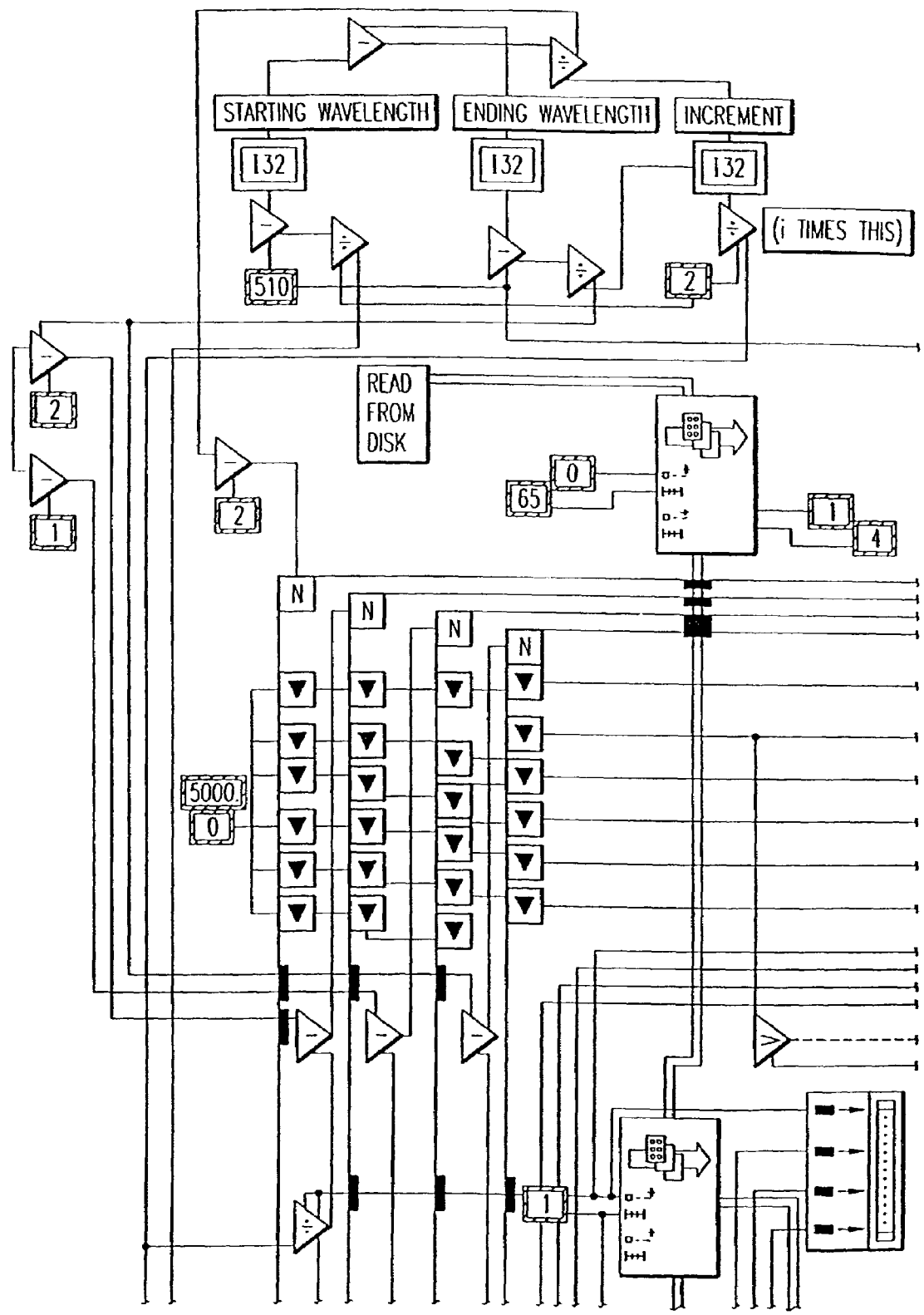
Figure 11B:
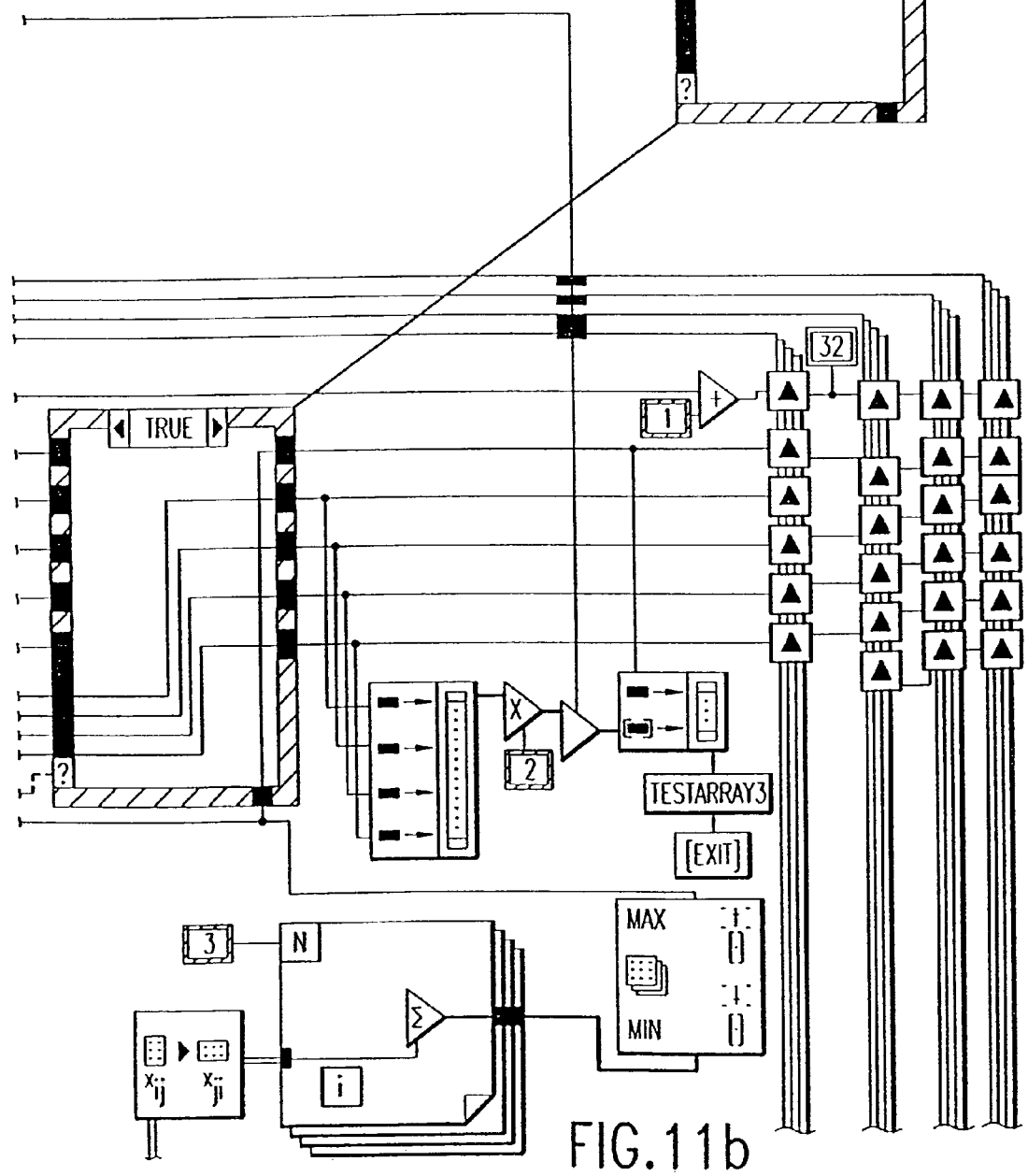
Figure 11C:
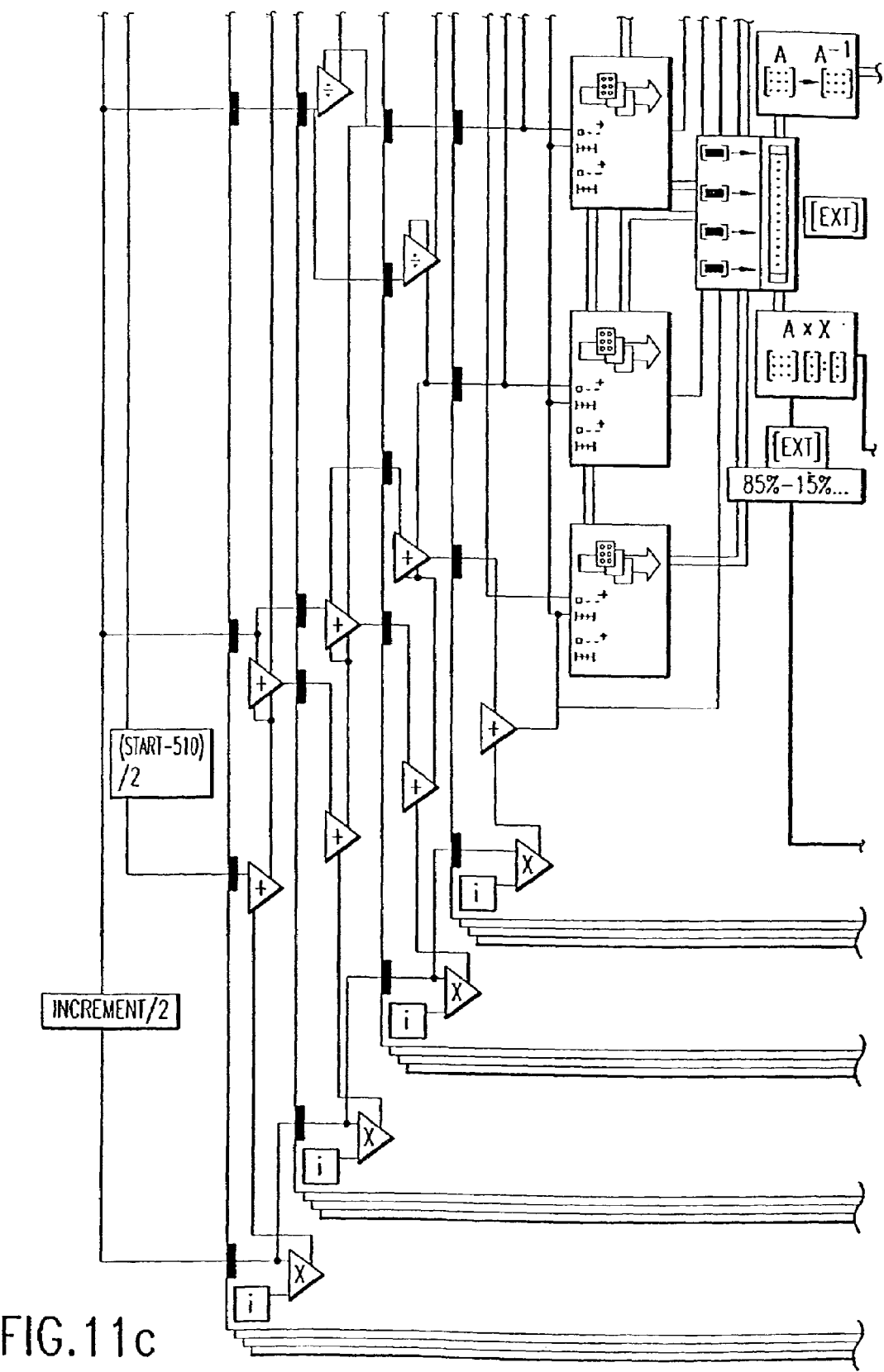
Figure 11D:
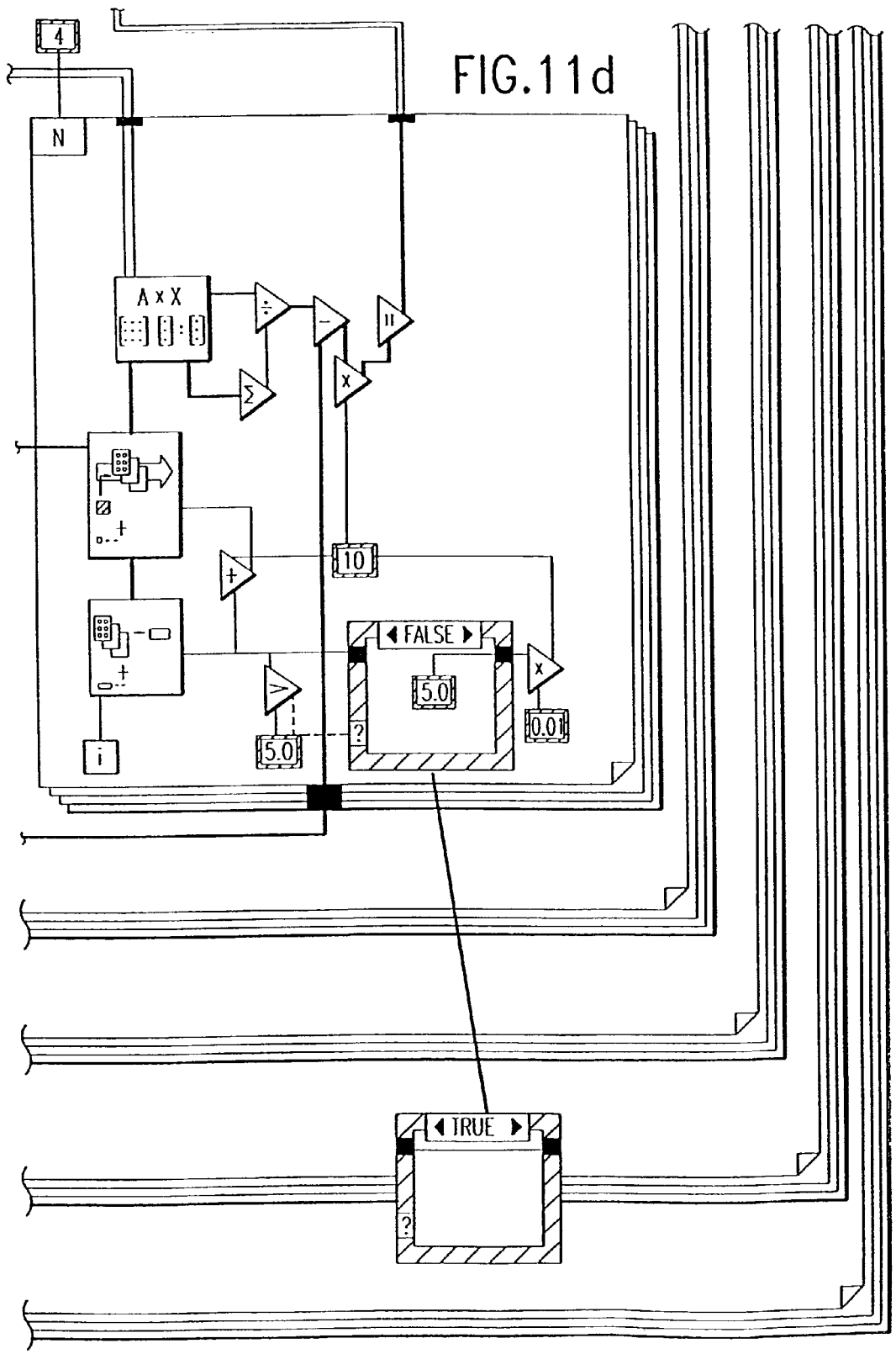

Referring now to FIG. 10, presented is a method of operating the apparatus of FIG. 6, in accordance with the present invention, to perform the light-scattering correction of Embodiment B.

Beginning in block 101, the counter n is initialized to zero. Then, in block 92, scattering vector $S_{RBC}$ is set equal to $S_{RBC}$(HbO$_2$) and $S_{NS}$ is set equal to $S_{NS}$(HbO$_2$). Then, in block 103 equation 6B is used to solve for [HbO$_2$], [HbCO], [Hi], [Hb], [br], $m_{RBCscat}$, and $m_{NSscat}$.

Then, control passes to block 104 where the counter n is incremented by one. In block 105, it is determined whether the counter n is greater than four. If not, control passes to block 106 where the quantities calculated for the concentrations in step 103 are inserted into equations 7B and 8B to compute a new value for $S_{RBC}$. Control then returns to block 103. If, on the other hand, decision block 105 determines that counter n is greater than four, control passes to decision block 107 where it is determined whether the spectral width is greater than 1 nm. If so, control passes to block 108 where the finite bandwidth correction of equation 9B is performed. Then, in block 109, the latest values for the concentrations of the six constituent components are reported. If, on the other hand, decision block 107 determines that the spectral width is not greater than 1 nm, control passes directly to block 109 for report of the concentrations.

Appendix B includes a source code listing in the C programming language which embodies the method of the flow chart of FIG. 10. In practice, the method of the flow chart of FIG. 10, embodied either in the source code program of Appendix B or an equivalent program, is used to program computer 13 of FIG. 6, to cause the apparatus of FIG. 6 to perform the method of Embodiment B to correct for light scattering.

Neither Embodiment A nor B allows the simultaneous use of the nonspecific scattering factor and the measurement of sulfhemoglobin. A third specific embodiment, Embodiment C, which utilizes one more wavelength than Embodiments A and B, accommodates both of these features. Embodiment C uses the same first seven wavelengths as do Embodiments A and B. In Embodiment C, the following rules hold: both light scattering by red blood cells and nonspecific light scattering are considered, and the concentrations of six compounds are measured, namely HbO$_2$, HbCO, Hi, Hb, SHb, and br.

In Embodiment C, the eighth wavelength is chosen so that the differences $e_{6HbO2}-e_{8HbO2}$, $e_{6HbCO}-e_{8HbCO}$, $e_{6Hi}-e_{8Hi}$, $e_{6Hb}-e_{8Hb}$, $e_{6br}-e_{8br}$, $e_{6RBC}-e_{8RBC}$, and $e_{6NS}-e_{8NS}$, are simultaneously small while $e_{6SHb}-e_{8SHb}$ is quite large, i.e., in the 635 to 645 nm range. The choice of the eighth wavelength, in view of the mathematical relationship between a matrix and its inverse, assures that the computation of sulfhemoglobin concentration is primarily dependent on the 6th and 8th wavelengths and is affected very little by the other six wavelengths. Embodiment C preferably uses 638 nm as its eighth wavelength. If the samarium-neon hollow-cathode lamp is used, the preferred eighth wavelength among its emission lines is 638.3 nm.

The relevant equations for Embodiment C are as follows:

EMBODIMENT C $$OD_{iabs} = e_{iHbO2}[\text{HbO}_2] + e_{iHbCO}[\text{HbCO}] + e_{iHi}[\text{Hi}] + e_{iHb}[\text{Hb}] + e_{iSHb}[\text{SHb}] + e_{ibr}[\text{br}] \tag{6C}$$

$$\begin{bmatrix} OD_1/d \\ OD_2/d \\ OD_3/d \\ OD_4/d \\ OD_5/d \\ OD_6/d \\ OD_7/d \\ OD_8/d \end{bmatrix} = \begin{bmatrix} e_{1HbO2} & e_{1HbCO} & e_{1Hi} & e_{1Hb} & e_{1SHb} & e_{1br} & s_{1RBC} & s_{1NS} \\ e_{2HbO2} & e_{2HbCO} & e_{2Hi} & e_{2Hb} & e_{2SHb} & e_{2br} & s_{2RBC} & s_{2NS} \\ e_{3HbO2} & e_{3HbCO} & e_{3Hi} & e_{3Hb} & e_{3SHb} & e_{3br} & s_{3RBC} & s_{3NS} \\ e_{4HbO2} & e_{4HbCO} & e_{4Hi} & e_{4Hb} & e_{4SHb} & e_{4br} & s_{4RBC} & s_{4NS} \\ e_{5HbO2} & e_{5HbCO} & e_{5Hi} & e_{5Hb} & e_{5SHb} & e_{5br} & s_{5RBC} & s_{5NS} \\ e_{6HbO2} & e_{6HbCO} & e_{6Hi} & e_{6Hb} & e_{6SHb} & e_{6br} & s_{6RBC} & s_{6NS} \\ e_{7HbO2} & e_{7HbCO} & e_{7Hi} & e_{7Hb} & e_{7SHb} & e_{7br} & s_{7RBC} & s_{7NS} \\ e_{8HbO2} & e_{8HbCO} & e_{8Hi} & e_{8Hb} & e_{8SHb} & e_{8br} & s_{8RBC} & s_{8NS} \end{bmatrix} \begin{bmatrix} [\text{HbO}_2] \\ [\text{HbCO}] \\ [\text{Hi}] \\ [\text{Hb}] \\ [\text{SHb}] \\ [\text{br}] \\ m_{RBCscat} \\ m_{NSscat} \end{bmatrix}$$

-continued $$\begin{bmatrix} s_{1RBC} \\ s_{2RBC} \\ s_{3RBC} \\ s_{4RBC} \\ s_{5RBC} \\ s_{6RBC} \\ s_{7RBC} \\ s_{8RBC} \end{bmatrix} = \begin{bmatrix} s_{1RBC}(HbO_2) & s_{1RBC}(HbCO) & s_{1RBC}(Hi) & s_{1RBC}(Hb) & s_{1RBC}(SHb) \\ s_{2RBC}(HbO_2) & s_{2RBC}(HbCO) & s_{2RBC}(Hi) & s_{2RBC}(Hb) & s_{2RBC}(SHb) \\ s_{3RBC}(HbO_2) & s_{3RBC}(HbCO) & s_{3RBC}(Hi) & s_{3RBC}(Hb) & s_{3RBC}(SHb) \\ s_{4RBC}(HbO_2) & s_{4RBC}(HbCO) & s_{4RBC}(Hi) & s_{4RBC}(Hb) & s_{4RBC}(SHb) \\ s_{5RBC}(HbO_2) & s_{5RBC}(HbCO) & s_{5RBC}(Hi) & s_{5RBC}(Hb) & s_{5RBC}(SHb) \\ s_{6RBC}(HbO_2) & s_{6RBC}(HbCO) & s_{6RBC}(Hi) & s_{6RBC}(Hb) & s_{6RBC}(SHb) \\ s_{7RBC}(HbO_2) & s_{7RBC}(HbCO) & s_{7RBC}(Hi) & s_{7RBC}(Hb) & s_{7RBC}(SHb) \\ s_{8RBC}(HbO_2) & s_{8RBC}(HbCO) & s_{8RBC}(Hi) & s_{8RBC}(Hb) & s_{8RBC}(SHb) \end{bmatrix} \begin{bmatrix} [HbO_2]/THb \\ [HbCO]/THb \\ [Hi]/THb \\ [Hb]/THb \\ [SHb]/THb \end{bmatrix} \quad (7C)$$

$$\begin{bmatrix} s_{1NS} \\ s_{2NS} \\ s_{3NS} \\ s_{4NS} \\ s_{5NS} \\ s_{6NS} \\ s_{7NS} \\ s_{8NS} \end{bmatrix} = \begin{bmatrix} s_{1NS}(HbO_2) & s_{1NS}(HbCO) & s_{1NS}(Hi) & s_{1NS}(Hb) & s_{1NS}(SHb) \\ s_{2NS}(HbO_2) & s_{2NS}(HbCO) & s_{2NS}(Hi) & s_{2NS}(Hb) & s_{2NS}(SHb) \\ s_{3NS}(HbO_2) & s_{3NS}(HbCO) & s_{3NS}(Hi) & s_{3NS}(Hb) & s_{3NS}(SHb) \\ s_{4NS}(HbO_2) & s_{4NS}(HbCO) & s_{4NS}(Hi) & s_{4NS}(Hb) & s_{4NS}(SHb) \\ s_{5NS}(HbO_2) & s_{5NS}(HbCO) & s_{5NS}(Hi) & s_{5NS}(Hb) & s_{5NS}(SHb) \\ s_{6NS}(HbO_2) & s_{6NS}(HbCO) & s_{6NS}(Hi) & s_{6NS}(Hb) & s_{6NS}(SHb) \\ s_{7NS}(HbO_2) & s_{7NS}(HbCO) & s_{7NS}(Hi) & s_{7NS}(Hb) & s_{7NS}(SHb) \\ s_{8NS}(HbO_2) & s_{8NS}(HbCO) & s_{8NS}(Hi) & s_{8NS}(Hb) & s_{8NS}(SHb) \end{bmatrix} \begin{bmatrix} [HbO_2]/THb \\ [HbCO]/THb \\ [Hi]/THb \\ [Hb]/THb \\ [SHb]/THb \end{bmatrix} \quad (8C)$$

$$\begin{bmatrix} [HbO_2]_{correction} \\ [HbCO]_{correction} \\ [Hi]_{correction} \\ [Hb]_{correction} \\ [SHb]_{correction} \\ [br]_{correction} \end{bmatrix} = \begin{bmatrix} a_{O2,O2} & a_{O2,CO} & a_{O2,Hi} & a_{O2,Hb} & a_{O2,SHb} & a_{O2,br} \\ a_{CO,O2} & a_{CO,CO} & a_{CO,Hi} & a_{CO,Hb} & a_{CO,SHb} & a_{CO,br} \\ a_{Hi,O2} & a_{Hi,CO} & a_{Hi,Hi} & a_{Hi,Hb} & a_{Hi,SHb} & a_{Hi,br} \\ a_{Hb,O2} & a_{Hb,CO} & a_{Hb,Hi} & a_{Hb,Hb} & a_{Hb,SHb} & a_{Hb,br} \\ a_{SHb,O2} & a_{SHB,CO} & a_{SHb,Hi} & a_{SHb,Hb} & a_{SHb,SHb} & a_{SHb,br} \\ a_{br,O2} & a_{br,CO} & a_{br,Hi} & a_{br,Hb} & a_{br,SHb} & a_{br,br} \end{bmatrix} \begin{bmatrix} [HbO_2] \\ [HbCO] \\ [Hi] \\ [Hb] \\ [SHb] \\ [br] \end{bmatrix} \quad (9C)$$

wherein [HbO$_2$], [HbCO], [Hi], [Hb], and [SHb] are the concentrations of the indicated hemoglobin species in the sample, $m_{RBCscat}$ and $m_{NSscat}$ are magnitudes of light scattering by the red blood cells and by the nonspecific factor, and THb=[HbO$_2$]+[HbCO]+[Hi]+[Hb]+[SHb]. OD$_1$, ..., OD$_8$ are the apparent optical densities of a sample of unaltered whole blood measured at each of the eight wavelengths, 488.4, 520.1, 562.4, 585.2, 597.5, 621.7, 671.7, and 638.3 nm, respectively.

Shown in the following addendum to Table I are the additional scattering parameters which are necessary (in addition to the parameters in Table I) for use in Embodiment C.

Addendum to Table I. Values for $S_{8NS}(\bullet)$, $S_{RBC}(\bullet)$, and $S_{NS}(SHb)$ for Embodiment C. In this addendum the indices 1, . . . , 8 refer specifically (and only) to the seven wavelengths 488.4, 520.1, 562.4, 585.2, 597.5, 621.7, 671.7, and 638.3 nm, respectively.

| $S_{8NS}(HbO_2)$ | $S_{8NS}(HbCO)$ | $S_{8NS}(Hi)$ | $S_{8NS}(Hb)$ | $S_{8NS}(SHb)$ |
|---|---|---|---|---|
| 1.379 | 0.682 | 22.259 | −7.463 | 22.259 |

| $S_{8RBC}(HbO_2)$ | $S_{8RBC}(HbCO)$ | $S_{8RBC}(Hi)$ | $S_{8RBC}(Hb)$ | $S_{8RBC}(SHb)$ |
|---|---|---|---|---|
| 1.051 | 1.117 | 1.000 | 1.202 | 1.000 |

| | |
|---|---|
| $S_{1NS}(SHb)$ | 6.216 |
| $S_{2NS}(SHb)$ | 6.629 |
| $S_{3NS}(SHb)$ | 7.065 |
| $S_{4NS}(SHb)$ | 7.200 |
| $S_{5NS}(SHb)$ | 8.944 |
| $S_{6NS}(SHb)$ | 21.220 |
| $S_{7NS}(SHb)$ | 2.800 |
| $S_{8NS}(SHb)$ | 22.259 |

6. COMPARATIVE EXAMPLE

To demonstrate the utility of the present invention in comparison with prior art, the Applicants made measurements of the concentrations of various hemoglobin species using a Radiometer OSM3 Hemoximeter and using the present invention. The Radiometer OSM3 employs an ultrasonic hemolyzer, and is believed to embody the optical geometry of Johansen et al. (U.S. Pat. No. 3,972,614), and the method and apparatus of Lundsgaard (U.S. Pat. No. 4,997,769) to correct for the turbidity of hemolyzed blood.

In normal operation, the OSM3 first ultrasonically hemolyses each sample, then makes measurements of the sample's optical absorbance at multiple wavelengths, and finally uses the method of Lundsgaard to correct for the residual turbidity of the hemolyzed sample. To determine whether the method and apparatus of Lundsgaard could accurately measure hemoglobin concentrations in unaltered whole blood, the Applicants analyzed blood samples with the OSM3 operating normally and then analyzed the same blood samples with the OSM3's ultrasonic hemolyzer disabled.

Table III shows that the Radiometer OSM3, believed to use the method and apparatus of Lundsgaard (U.S. Pat. No. 4,997,769), gives completely erroneous results when the blood sample is not hemolyzed. For example, measurements of the total hemoglobin concentrations with and without hemolysis differ by as much as 7.4 grams/dl. Similarly, it is physically impossible for the relative concentration of oxyhemoglobin to be 400% or for the concentration of carboxyhemoglobin to be negative (−99%). Thus, it is readily apparent that the method and apparatus of Lundsgaard fail to yield even plausible results on unaltered, whole blood.

TABLE III

Performance of the Radiometer OSM3 (Lundsgaard method) on hemolyzed and unaltered, whole blood.

| Sample # | Hemolyzer ON | | | | Hemolyzer OFF | | | |
|---|---|---|---|---|---|---|---|---|
| | THb | HbO2 | HbCO | HbMet | THb | HbO2 | HbCO | HbMet |
| 1 | 18.2 | 88.8 | 5.5 | 0.5 | 11.8 | 159.8 | −68.5 | −37.1 |
| 2 | 8.2 | 82.3 | −0.2 | 0.6 | 1.8 | 422.0 | −99.9 | −99.9 |
| 3 | 17.1 | 98.4 | −0.4 | 0.2 | 13.2 | 142.6 | −44.6 | −19.5 |
| 4 | 18.4 | 76.1 | −0.6 | 0.2 | 14.4 | 130.9 | −45.3 | −18.8 |
| 5 | 13.4 | 90.4 | −0.1 | 0.4 | 6.3 | 211.8 | −99.9 | −55.0 |
| 6 | 18.3 | 88.0 | −0.5 | 0.3 | 14.1 | 135.2 | −45.6 | −19.0 |
| 7 | 18.9 | 74.4 | 0.2 | 0.1 | 14.4 | 118.7 | −38.6 | −17.2 |
| 8 | 13.7 | 53.7 | −0.2 | 0.1 | 8.0 | 127.9 | −93.5 | −43.6 |
| 9 | 15.5 | 87.5 | −0.6 | 0.4 | 10.2 | 156.6 | −73.7 | −33.7 |
| 10 | 14.0 | 95.4 | −0.3 | 0.5 | 6.6 | 233.8 | −99.9 | −66.8 |
| 11 | 13.2 | 57.1 | 0.3 | 0.5 | 7.9 | 138.1 | −89.5 | −40.3 |
| 12 | 12.3 | 95.8 | −0.5 | 0.5 | 7.8 | 172.9 | −75.5 | −32.8 |

To evaluate the present invention's ability to make accurate measurements directly on unaltered, whole blood, the Applicants employed the herein described methods and apparatus that constitute the present invention and made measurements of the concentrations of various hemoglobin species in blood samples before and after hemolysis. The results appear in Table IV.

TABLE IV

Performance of the present invention on hemolyzed and unaltered, whole blood.

| Sample # | Hemolyzed | | | | Unaltered | | | |
|---|---|---|---|---|---|---|---|---|
| | THb | HbO2 | HbCO | HbMet | THb | HbO2 | HbCO | HbMet |
| 1 | 10.4 | 97.8 | 1.3 | 0.4 | 10.2 | 98.8 | 1.6 | 0.2 |
| 2 | 13.6 | 98.0 | 1.2 | 0.2 | 14.3 | 97.6 | 1.1 | 0.5 |
| 3 | 14.6 | 98.3 | 2.3 | −0.2 | 14.3 | 98.2 | 1.9 | 0.2 |
| 4 | 11.1 | 98.8 | 0.4 | 0.0 | 11.0 | 98.9 | 0.7 | −0.2 |
| 5 | 14.0 | 97.0 | 3.1 | 0.0 | 13.3 | 97.8 | 2.3 | 0.2 |
| 6 | 13.3 | 97.6 | 0.6 | 0.7 | 12.9 | 97.6 | 1.1 | 0.5 |
| 7 | 17.9 | 98.1 | 1.4 | 0.1 | 17.8 | 98.2 | 0.9 | 0.3 |
| 8 | 15.5 | 97.7 | 2.2 | 0.3 | 16.0 | 98.3 | 2.0 | 0.1 |
| 9 | 13.3 | 98.3 | 2.0 | 0.0 | 13.3 | 98.7 | 1.3 | 0.2 |
| 10 | 18.7 | 97.8 | 2.0 | 0.1 | 19.0 | 98.5 | 1.3 | 0.1 |
| 11 | 16.0 | 97.1 | 0.9 | 0.5 | 16.0 | 97.1 | 1.2 | 0.4 |
| 12 | 17.5 | 98.2 | 2.0 | 0.1 | 17.5 | 98.4 | 1.7 | 0.2 |

Table IV shows that the measured total hemoglobin concentrations with and without hemolysis typically differ by only a few tenths of a gram/dl. Similarly, the measurements of the relative concentrations of oxy-, carboxy-, and methemoglobin are consistently in close agreement in all of the samples. In summary, the results shown in Tables III and IV demonstrate conclusively that the present invention enables one skilled in the art to make accurate measurements of the hemoglobin concentrations directly in unaltered, whole blood; whereas the method and apparatus of Lundsgaard fail to obtain satisfactory results.

While the present invention has been described in connection with preferred embodiments, it will be understood that these embodiments are only examples, and should not be considered a limitation of the present invention.

APPENDIX A

COPYRIGHT, 1992, BOARD OF REGENTS, THE UNIVERSITY OF TEXAS SYSTEM

```
/*****************************************************************/
/* FUNCTIONS: 1) void slope_comp_LED( )          */
/*            2) void OD_to_7sat_LED( )          */
/*            3) void slope_recur_LED( )         */
/*****************************************************************/
#include "C:\ATG\A VOX\C_PROG\TYPE\A VOX_TYP.C"
#include "C:\ATG\A VOX\C_PROG\DEF\A VOX_DEF.C"
#include "C:\ATG\A VOX\C_PROG\MATH\MATH_DEF.C"
#include "C:\ATG\A VOX\C_PROG\HDR\A VOX_HDR.C"
extern const vector Insats_vec;
extern const matrix Identity_mtx;
extern const matrix Scat_mtx;
extern const matrix Sulf_mtx;
extern const matrix THbslp_mtx;
void slope_comp_LED(Xinsat,Xscat,Xsulf,XTHb)
      vector *Xinsat; /* Xinsat (Input) = 'Initial %Sats'   */
      vector *Xscat;  /* Xscat (Output) = 'Scat Slopes (Vector)'*/
      vector *Xsulf;  /* Xsulf (Output) = 'Sulf Slopes (Vector)'*/
      vector *XTHb;   /* XTHb (Output) = 'THb Slopes (Vector)'*/
{
      AtimesX((matrix *)Scat_mtx,Xinsat,Xscat);
      AtimesX((matrix *)Sulf_mtx,Xinsat,Xsulf);
      AtimesX((matrix *)THbslp_mtx,Xinsat,XTHb);
      return;
} /* end slope_comp_LED( ) */
void OD_to_7sat_LED(AExtC2,ACalS,ACsats,XODs,XSHbs,Xsats,XScatCF,Xsats1P,
                    xTotHb,xTHbc,EnSlp,EnTHb,En Ver)
      matrix *AExtC2; /* AExtC2 (Input) = 'Extinction Coeffs.2' */
      matrix *ACalS;  /* ACalS (Input) = 'Calibration Sats'   */
      matrix *ACsats; /* ACsats (Input) = 'Computed Sats'     */
      vector *XODs;   /* XODs (Input) = 'ODs'                 */
      vector *XSHbs;  /* XSHbs (Output) = 'SHb Correction Factors' */
      vector *Xsats;  /* Xsats (Output) = 'SATS'              */
      vector *XScatCF; /* XScatCF (Output) = 'Scattering Corr'n Fac.' */
      vector *Xsats1P; /* Ssats1P (Output) = 'SATS.1st.Pass'  */
      l_real *xTotHb; /* xTotHb (Output) = 'Total Hb'         */
      l_real xTHbc;   /* xTHbc (Input) = 'THb constant'       */
      boolean EnSlp;  /* EnSlp (Input) = 'Enable Slopes'      */
      boolean EnTHb;  /* EnTHb (Input) = 'Enable THb Slopes'  */
      boolean EnVer,  /* EnVer (Input) = 'Black-Old version; Wht-'*/
}
      matrix Atmp1,Atmp2,Atmp3;
      vector Xtmp1,Xtmp2,Xtmp3,Xtmp4,Xtmp5,Xtmp6,Xtmp7,Xtmp8;
      l_real xtmp1,xtmp2,xtmp3,xtmp4,xtmp5,xtmp6,xtmp7,xtmp8,xtmp9,xsum;
      l_real sulf_thb_cutoff, sulf_slp_cutoff;
      boolean enable_slp, enable_thb_slp;
      Ainverse((matrix *)ACalS,(matrix *)Atmp1);
      AtimesB((matrix *)Atmp1,(matrix *)ACats,(matrix *)Atmp2);
      AtimesB((matrix *)Atmp2,(matrix *)AExtC2,(matrix *)Atmp1);
      Atranspose((matrix *)Atmp1,(matrix *)Atmp2);
      Ainverse((matrix *)Atmp2,(matrix *)Atmp3);
      /* switch and calculate Y from XODs - do not change Atmp3 yet */
      xtmp1 = getXvalue((vector *)XODs,0);
      xtmp2 = x_abs(xtmp1);
      xtmp3 = xtmp1 / xtmp2;
      Xtimesx((vector *)XODs,xtmp3,(vector *)Xtmp1); /* Xtmp1 = Y */
      AtimesX((matrix *)Atmp3,(vector *)Xtmp1,(vector *)Xtmp2); /* may discard Atmp3 now */
      Xsubset((vector *)Xtmp2,0,5,(vector *)Xtmp3);
      xsum = Xsum((vector *)Xtmp3);
      Xdivx((vector *)Xtmp2,xsum,(vector *)Xtmp 1);
      eep_set_var((u_long)&enable_slp,"Enable_Slopes");
      eep_set_var((u_long)&enable_thb_slp,"Enable_THb_Slopes");
      sulf_thb_cutoff = (l_real)- 1.0;
      sulf_slp_cutoff = (l_real)- 1.0;
      /*********************************************/
      /* slope_recur_LED #1              */
      /* parameter = variable IO         */
      /* Xsatsf   = Xtmp1                */
      /* Xconc    = Xtmp2                */
      /* Xscat    = Xtmp3 (output-discarded) */
      /* Xsulf    = Xtmp4 (output-discarded) */
      /* Xsats    = Xtmp5                */
      /* xsulfTHb = sulf_thb_cutoff      */
      /* xsulfslp = sulf_slp_cutoff      */
      /* xTHbc    = xTHbc                */
      /* EnSlp    = enable_slp           */
      /* EnTHb    = enable_thb_slp       */
      /*********************************************/
```

APPENDIX A-continued

```
slope_recur_LED((vector *)Xtmp1,
                (vector *)Xtmp2,
                (vector *)Xtmp3,
                (vector *)Xtmp4,
                (vector *)Xtmp5,
                (l_real)sulf_thb_cutoff,
                (l_real)sulf_slp_cutoff,
                (l_real)xTHbc,
                (boolean)enable_slp,
                (boolean)enable_thb_slp);
Xtimesx((vector *)Xtmp5,(l_real)100.0,(vector *)Xsats1P); /* define SATS.1st.Pass */
/**********************************/
/* slope_recur_LED #2      */
/* parameter = variable IO */
/* Xsatsf   = Xtmp5        */
/* Xconc    = Xtmp2        */
/* Xscat    = Xtmp7        */
/* Xsulf    = Xtmp8        */
/* Xsats    = Xtmp1        */
/* xsulfTHb = sulf_thb_cutoff*/
/* xsulfslp = sulf_slp_cutoff*/
/* xTHbc    = xTHbc        */
/* EnSlp    = enable_slp   */
/* EnTHb    = enable_thb_slp */
/**********************************/
slope_recur_LED((vector *)Xtmp5,
                (vector *)Xtmp2,
                (vector *)Xtmp7,
                (vector *)Xtmp8,
                (vector *)Xtmp1,
                (l_real)sulf_thb_cutoff,
                (l_real)sulf_slp_cutoff,
                (l_real)xTHbc,
                (boolean)enable_slp,
                (boolean)enable_thb_slp);
/**********************************************/
/* slope_recur_LED #3                 */
/* parameter = variable IO            */
/* Xsatsf   = Xtmp1                   */
/* Xconc    = Xtmp2                   */
/* Xscat    = Xtmp3 (output-discarded) */
/* Xsulf    = Xtmp4 (output-discarded) */
/* Xsats    = Xtmp5                   */
/* xsulfTHb = sulf_thb_cutoff         */
/* xsulfslp = sulf_slp_cutoff         */
/* xTHbc    = xTHbc                   */
/* EnSlp    = enable_slp              */
/* EnTHb    = enable_thb_slp          */
/**********************************************/
slope_recur_LED((vector *)Xtmp1,
                (vector *)Xtmp2,
                (vector *)Xtmp3,
                (vector *)Xtmp4,
                (vector *)Xtmp5,
                (l_real)sulf_thb_cutoff,
                (l_real)sulf_slp_cutoff,
                (l_real)xTHbc,
                (boolean)enable_slp,
                (boolean)enable_thb_slp);
/**********************************/
/* slope_recur_LED #4      */
/* parameter = variable IO */
/* Xsatsf   = Xtmp5        */
/* Xconc    = Xtmp2        */
/* Xscat    = Xtmp7        */
/* Xsulf    = Xtmp8        */
/* Xsats    = Xtmp1        */
/* xsulfTHb = sulf_thb_cutoff*/
/* xsulfslp = sulf_slp_cutoff*/
/* xTHbc    = xTHbc        */
/* EnSlp    = enable_slp   */
/* EnTHb    = enable_thb_slp */
/**********************************/
slope_recur_LED((vector *)Xtmp5,
                (vector *)Xtmp2,
                (vector *)Xtmp7,
                (vector *)Xtmp8,
                (vector *)Xtmp1,
                (l_real)sulf_thb_cutoff,
```

APPENDIX A-continued

```
                        (l_real)sulf_slp_cutoff,
                        (l_real)xTHbc,
                        (boolean)enable_slp,
                        (boolean)enable_thb_slp);
        Xsubset((vector *)Xtmp5,0,4,(vector *)Xtmp3);
        Xtimesx((vector *)Xtmp1,(l_real)100.0,(vector *)Xsats); /* define Xsats */
        Xclear((vector *)Xtmp6);
        Xtmp6[0] = (l_real)0.020;
        Xtmp6[1] = (l_real)0.020;
        Xtmp6[2] = (l_real)0.000;
        Xtmp6[3] = (l_real)0.016;
        xtmp4 = XY_inproduct((vector *)Xtmp3,(vector *)Xtmp6);
        xtmp1 = Xtmp2[6];
        xtmp7 = xtmp1 * xtmp4;
        xtmp8 = Xtmp2[4];
        xtmp9 = xtmp7 + xtmp8;
        xtmp4 = xtmp9 / xsum; /* xtmp4 gets compared to -1.0 */
        Xclear((vector *)Xtmp7);
        Xtmp7[0] = (l_real)-7.50;
        Xtmp7[1] = (l_real)-2.50;
        Xtmp7[2] = (l_real) 0.00;
        Xtmp7[3] = (l_real)12.00;
        xtmp5 = XY_inproduct((vector *)Xtmp3,(vector *)Xtmp7);
        Xclear((vector *)Xtmp8);
        Xtmp8[0] = (l_real)-0.280;
        Xtmp8[1] = (l_real)-0.280;
        Xtmp8[2] = (l_real) 0.000;
        Xtmp8[3] = (l_real)-0.150;
        xtmp6 = XY_inproduct((vector *)Xtmp3,(vector *)Xtmp8);
        if(EnSlp == FALSE) {
                xtmp5 = (l_real)0.0;
                xtmp6 = (l_real)0.0;
        } /* end if Enable Slopes is FALSE */
        if(xtmp4 > (l_real)-1.0) { xtmp5 = (l_real)0.0; }
        xtmp4 = xtmp5 * xtmp9;
        xtmp2 = xtmp6 * xtmp1;
        xtmp3 = xtmp4 + xtmp2;
        xtmp4 = xsum + xtmp3;
        *xTotHb = xTHbc * xtmp4;
        return;
} /* end OD_to_7sat_LED( ) */
void slope_recur_LED(Xsatsf, Xconc, Xscat, Xsulf, Xsats, xsulfTHb,
                                xsulfslp, xTHbc, EnSlp, EnTHb)
        vector *Xsatsf; /* Xsatsf (Input) = 'Sats (fractional)' */
        vector *Xconc; /* Xconc (Input) = 'Concentrations'   */
        vector *Xscat; /* Xscat (Output) = 'Scat slopes'   */
        vector *Xsulf; /* Xsulf (Output) = 'Sulf slopes'   */
        vector *Xsats; /* Xsats (Output) = 'SATS' */
        l_real xsulfTHb; /* xsulfTHb (Input) = 'Sulf THb Cut-off' */
        l_real xsulfslp; /* xsulfslp (Input) = 'Sulf Slope Cut-off' */
        l_real xTHbc; /* xTHbc (Input) = 'THb constant'   */
        boolean EnSlp; /* EnSlp (Input) = 'Enable Slopes'   */
        boolean EnTHb; /* EnTHb (Input) = 'Enable THb Slopes' */
{
        vector Xtmp1,Xtmp2,Xtmp3,Xtmp4;
        l_real xtmp1,xtmp2,xtmp3,xsum;
        long int1;
        /* function call: slope_comp_LED( ) */
        /* parameter = variable I/O   */
        /* Xinsat   = Xsatsf I        */
        /* Xscat    = Xscat O         */
        /* Xsulf    = Xsulf O         */
        /* XTHb     = Xtmp1 O         */
        slope_comp_LED((vector *)Xsatsf,(vector *)Xscat,(vector *)Xsulf,(vector *)Xtmp1);
        if(EnTHb == TRUE) { xtmp1 = (l_real)1.0; }
        else{           xtmp1 = (l_real)0.0; }
        Xtimesx((vector *)Xtmp1,xtmp1,(vector *)Xtmp2);
        Xsubset((vector *)Xconc,0,5,(vector *)Xtmp3);
        xsum = Xsum((vector *)Xtmp3);
        xtmp1 = xTHbc * xsum;
        xtmp2 = xtmp1 - (l_real)13.5;
        Xtimesx((vector *)Xtmp2,xtmp2,(vector *)Xtmp1);
        Xdivx((vector *)Xtmp1,(l_real)100.0,(vector *)Xtmp3); /* save Xtmp3 */
        if(EnSlp == TRUE) { xtmp1 = (l_real)1.0; }
        else{           xtmp1 = (l_real)0.0; }
        Xtimesx((vector *)Xscat,xtmp1,(vector *)Xtmp1);
        xtmp2 = getXvalue((vector *)Xconc,6);
        Xtimesx((vector *)Xtmp1,xtmp2,(vector *)Xtmp2);
        XplusY((vector *)Xtmp2,(vector *)Xconc,(vector *)Xtmp1);
```

APPENDIX A-continued

```
        xtmp3 = getXvalue((vector *)Xtmp1,4);
        xtmp2 = xtmp3 / xsum;
        if(xtmp2 > xsulfTHb) { int1 = 5; }
        else{           int1 = 4; }
        if(xtmp2 > xsulfslp) { xtmp2 = (l_real)0.0; }
        else{           xtmp2 = (l_real)1.0; }
        Xtimesx((vector *)Xsulf,xtmp1,(vector *)Xtmp4);
        Xtimesx((vector *)Xtmp4,xtmp2,(vector *)Xtmp2);
        Xtimesx((vector *)Xtmp2,xtmp3,(vector *)Xtmp4);
        XplusY((vector *)Xtmp1,(vector *)Xtmp4,(vector *)Xtmp2);
        Xsubset((vector *)Xtmp2,0,int1,(vector *)Xtmp1);
        xtmp3 = Xsum((vector *)Xtmp1);
        Xdivx((vector *)Xtmp2,xtmp3,(vector *)Xtmp4);
        xtmp1 = Xtmp2[5];
        xtmp2 = xTHbc * xtmp1;
        Xtmp4[5] = xtmp2;       /* place value into vector */
        XplusY((vector *)Xtmp3,(vector *)Xtmp4,(vector *)Xsats);
        return;
} /* end slope_recur_LED( ) */
/* END FILE: MTX_COMP.C */
```

APPENDIX B

COPYRIGHT, 1992, BOARD OF REGENTS, THE UNIVERSITY OF TEXAS SYSTEM

```
/****************************************************/
/* FUNCTIONS: 1) void slope_comp_LED( )             */
/*            2) void OD_to_7sat_LED( )             */
/*            3) void slope_recur_LED( )            */
/****************************************************/
#include "C:\ATG\A VOX\C_PROG\TYPE\A VOX_TYP.C"
#include "C:\ATG\A VOX\C_PROG\DEF\A VOX_DEF.C"
#include "C:\ATG\A VOX\C_PROG\MATH\MATH_DEF.C"
#include "C:\ATG\A VOX\C_PROG\HDR\A VOX_HDR.C"
extern const vector Insats_vec;
extern const matrix Identity_mtx;
extern const matrix Scat_mtx;
extern const matrix Sulf_mtx;
extern const matrix THbslp_mtx;
void slope_comp_LED(Xinsat,Xscat,Xsulf,XTHb)
        vector *Xinsat; /* Xinsat (Input) = 'Initial %Sats'   */
        vector *Xscat;  /* Xscat (Output) = 'Scat Slopes (Vector)' */
        vector *Xsulf;  /* Xsulf (Output) = 'Sulf Slopes (Vector)' */
        vector *XTHb;   /* XTHb (Output) = 'THb Slopes (Vector)' */
{
        AtimesX((matrix *)Scat_mtx,Xinsat,Xscat);
        AtimesX((matrix *)Sulf_mtx,Xinsat,Xsulf);
        AtimesX((matrix *)THbslp_mtx,Xinsat,XTHb);
        return;
} /* end slope_comp_LED( ) */
void OD_to_7sat_LED(AExtC2,ACalS,ACsats,XODs,XSHbs,Xsats,XScatCF,Xsats1P,
                    xTotHb,xTHbc,EnSlp,EnTHb,EnVer)
        matrix *AExtC2; /* AExtC2 (Input) = 'Extinction Coeffs.2' */
        matrix *ACalS;  /* ACalS (Input) = 'Calibration Sats'   */
        matrix *ACsats; /* ACsats (Input) = 'Computed Sats'     */
        vector *XODs;   /* XODs (Input) = 'ODs'                 */
        vector *XSHbs;  /* XSHbs (Output) = 'SHb Correction Factors' */
        vector *Xsats;  /* Xsats (Output) = 'SATS'              */
        vector *XScatCF;/* XScatCF (Output) = 'Scattering Corr'n Fac.' */
        vector *Xsats1P;/* Ssats1P (Output) = 'SATS.1st.Pass'    */
        l_real *xTotHb; /* xTotHb (Output) = 'Total Hb'          */
        l_real xTHbc;   /* xTHbc (Input) = 'THb constant'        */
        boolean EnSlp;  /* EnSlp (Input) = 'Enable Slopes'       */
        boolean EnTHb;  /* EnTHb (Input) = 'Enable THb Slopes'   */
        boolean EnVer;  /* EnVer (Input) = 'Black-Old version; Wht-'*/
{
        matrix Atmp1,Atmp2,Atmp3;
        vector Xtmp1,Xtmp2,Xtmp3,Xtmp4,Xtmp5,Xtmp6,Xtmp7,Xtmp8;
        l_real xtmp1,xtmp2,xtmp3,xtmp4,xtmp5,xtmp6,xtmp7,xtmp8,xtmp9,xsum;
        l_real sulf_thb_cutoff,sulf_slp_cutoff;
        boolean enable_slp, enable_thb_slp;
        Ainverse((matrix *)ACalS,(matrix *)Atmp1);
        AtimesB((matrix *)Atmp1,(matrix *)ACsats,(matrix *)Atmp2);
        AtimesB((matrix *)Atmp2,(matrix *)AExtC2,(matrix *)Atmp1);
        Atranspose((matrix *)Atmp1,(matrix *)Atmp2);
        Ainverse((matrix *)Atmp2,(matrix *)Atmp3);
        /* switch and calculate Y from XODs - do not change Atmp3 yet */
```

APPENDIX B-continued

```
xtmp1 = getXvalue((vector *)XODs,0);
xtmp2 = x_abs(xtmp1);
xtmp3 = xtmp1 / xtmp2;
Xtimesx((vector *)XODs,xtmp3,(vector *)Xtmp1); /* Xtmp1 = Y */
AtimesX((matrix *)Atmp3,(vector *)Xtmp1,(vector *)Xtmp2); /* may discard Atmp3 now */
Xsubset((vector *)Xtmp2,0,5,(vector *)Xtmp3);
xsum = Xsum((vector *)Xtmp3);
Xdivx((vector *)Xtmp2,xsum,(vector *)Xtmp1);
eep_set_var((u_long)&enable_slp,"Enable_Slopes");
eep_set_var((u_long)&enable_thb_slp,"Enable_THb_Slopes");
sulf_thb_cutoff = (l_real)1.25;
sulf_slp_cutoff = (l_real)1.25;
/******************************************/
/* slope_recur_LED #1                     */
/* parameter = variable IO                */
/* Xsatsf   = Xtmp1                       */
/* Xconc    = Xtmp2                       */
/* Xscat    = Xtmp3 (output-discarded)    */
/* Xsulf    = Xtmp4 (output-discarded)    */
/* Xsats    = Xtmp5                       */
/* xsulfTHb = sulf_thb_cutoff             */
/* xsulfslp = sulf_slp_cutoff             */
/* xTHbc    = xTHbc                       */
/* EnSlp    = enable_slp                  */
/* EnTHb    = enable_thb_slp              */
/******************************************/
slope_recur_LED((vector *)Xtmp1,
                (vector *)Xtmp2,
                (vector *)Xtmp3,
                (vector *)Xtmp4,
                (vector *)Xtmp5,
                (l_real)sulf_thb_cutoff,
                (l_real)sulf_slp_cutoff,
                (l_real)xTHbc,
                (boolean)enable_slp,
                (boolean)enable_thb_slp);
Xtimesx((vector *)Xtmp5,(l_real)100.0,(vector *)Xsats1P); /* define SATS.1st.Pass */
/******************************************/
/* slope_recur_LED #2                     */
/* parameter = variable IO                */
/* Xsatsf   = Xtmp5                       */
/* Xconc    = Xtmp2                       */
/* Xscat    = Xtmp7                       */
/* Xsulf    = Xtmp8                       */
/* Xsats    = Xtmp1                       */
/* xsulfTHb = sulf_thb_cutoff*/
/* xsulfslp = sulf_slp_cutoff*/
/* xTHbc    = xTHbc                       */
/* EnSlp    = enable_slp   */
/* EnTHb    = enable_thb_slp */
/******************************************/
slope_recur_LED((vector *)Xtmp5,
                (vector *)Xtmp2,
                (vector *)Xtmp7,
                (vector *)Xtmp8,
                (vector *)Xtmp1,
                (l_real)sulf_thb_cutoff,
                (l_real)sulf_slp_cutoff,
                (l_real)xTHbc,
                (boolean)enable_slp,
                (boolean)enable_thb_slp);
/******************************************/
/* slope_recur_LED #3                     */
/* parameter = variable IO                */
/* Xsatsf   = Xtmp1                       */
/* Xconc    = Xtmp2                       */
/* Xscat    = Xtmp3 (output-discarded)    */
/* Xsulf    = Xtmp4 (output-discarded)    */
/* Xsats    = Xtmp5                       */
/* xsulfTHb = sulf_thb_cutoff             */
/* xsulfslp = sulf_slp_cutoff             */
/* xTHbc    = xTHbc                       */
/* EnSlp    = enable_slp                  */
/* EnTHb    = enable_thb_slp              */
/******************************************/
slope_recur_LED((vector *)Xtmp1,
                (vector *)Xtmp2,
                (vector *)Xtmp3,
                (vector *)Xtmp4,
```

APPENDIX B-continued

```
                            (vector *)Xtmp5,
                            (l_real)sulf_thb_cutoff,
                            (l_real)sulf_slp_cutoff,
                            (l_real)xTHbc,
                            (boolean)enable_slp,
                            (boolean)enable_thb_slp);
/***********************************/
/* slope_recur_LED #4            */
/* parameter = variable IO       */
/* Xsatsf    = Xtmp5             */
/* Xconc     = Xtmp2             */
/* Xscat     = Xtmp7             */
/* Xsulf     = Xtmp8             */
/* Xsats     = Xtmp1             */
/* xsulfTHb  = sulf_thb_cutoff*/
/* xsulfslp  = sulf_slp_cutoff*/
/* xTHbc     = xTHbc             */
/* EnSlp     = enable_slp  */
/* EnTHb     = enable_thb_slp */
/***********************************/
    slope_recur_LED((vector *)Xtmp5,
                            (vector *)Xtmp2,
                            (vector *)Xtmp7,
                            (vector *)Xtmp8,
                            (vector *)Xtmp1,
                            (l_real)sulf_thb_cutoff,
                            (l_real)sulf_slp_cutoff,
                            (l_real)xTHbc,
                            (boolean)enable_slp,
                            (boolean)enable_thb_slp);
    Xsubset((vector *)Xtmp5,0,4,(vector *)Xtmp3);
    Xtimesx((vector *)Xtmp1,(l_real)100.0,(vector *)Xsats); /* define Xsats */
    Xclear((vector *)Xtmp6);
    Xtmp6[0] = (l_real)0.020;
    Xtmp6[1] = (l_real)0.020;
    Xtmp6[2] = (l_real)0.000;
    Xtmp6[3] = (l_real)0.016;
    xtmp4 = XY_inproduct((vector *)Xtmp3,(vector *)Xtmp6);
    xtmp1 = Xtmp2[6];
    xtmp7 = xtmp1 * xtmp4;
    xtmp8 = Xtmp2[4];
    xtmp9 = xtmp7 + xtmp8;
    xtmp4 = xtmp9 / xsum; /* xtmp4 gets compared to 1.25 */
    Xclear((vector *)Xtmp7);
    Xtmp7[0] = (l_real)-7.50;
    Xtmp7[1] = (l_real)-2.50;
    Xtmp7[2] = (l_real) 0.00;
    Xtmp7[3] = (l_real) 12.00;
    xtmp5 = XY_inproduct((vector *)Xtmp3,(vector *)Xtmp7);
    Xclear((vector *)Xtmp8);
    Xtmp8[0] = (l_real)-0.280;
    Xtmp8[1] = (l_real)-0.280;
    Xtmp8[2] = (l_real) 0.000;
    Xtmp8[3] = (l_real)-0.150;
    xtmp6 = XY_inproduct((vector *)Xtmp3,(vector *)Xtmp8);
    if(EnSlp == FALSE){
        xtmp5 = (l_real)0.0;
        xtmp6 = (l_real)0.0;
    } /* end if Enable Slopes is FALSE */
    if(xtmp4 > (l_real)1.25){ xtmp5 = (l_real)0.0; }
    xtmp4 = xtmp5 * xtmp9;
    xtmp2 = xtmp6 * xtmp1;
    xtmp3 = xtmp4 + xtmp2;
    xtmp4 = xsum + xtmp3;
    *xTotHb = xTHbc * xtmp4;
    return;
} /* end OD_to_7sat_LED( ) */
void slope_recur_LED(Xsatsf, Xconc, Xscat, Xsulf, Xsats, xsulfTHb,
                            xsulfslp, xTHbc, EnSlp, EnTHb)
    vector *Xsatsf; /* Xsatsf (Input) = 'Sats (fractional)' */
    vector *Xconc;  /* Xconc (Input)  = 'Concentrations' */
    vector *Xscat;  /* Xscat (Output) = 'Scat slopes'   */
    vector *Xsulf;  /* Xsulf (Output) = 'Sulf slopes'   */
    vector *Xsats;  /* Xsats (Output) = 'SATS'          */
    l_real xsulfTHb; /* xsulfTHb (Input) = 'Sulf THb Cut-off' */
    l_real xsulfslp; /* xsulfslp (Input) = 'Sulf Slope Cut-off' */
    l_real xTHbc;   /* xTHbc (Input) = 'THb constant'   */
    boolean EnSlp;  /* EnSlp (Input) = 'Enable Slopes'  */
    boolean EnTHb;  /* EnTHb (Input) = 'Enable THb Slopes' */
```

APPENDIX B-continued

```
{
    vector Xtmp1,Xtmp2,Xtmp3,Xtmp4;
    l_real xtmp1,xtmp2,xtmp3,xsum;
    long int1;
    /* function call: slope_comp_LED( ) */
    /* parameter = variable I/O   */
    /* Xinsat = Xsatsf I          */
    /* Xscat = Xscat O            */
    /* Xsulf = Xsulf O            */
    /* XTHb = Xtmp1 O             */
    slope_comp_LED((vector *)Xsatsf,(vector *)Xscat,(vector *)Xsulf,(vector *)Xtmp1);
    if(EnTHb == TRUE) { xtmp1 = (l_real)1.0; }
    else{          xtmp1 = (l_real)0.0; }
    Xtimesx((vector *)Xtmp1,xtmp1,(vector *)Xtmp2);
    Xsubset((vector *)Xconc,0,5,(vector *)Xtmp3);
    xsum = Xsum((vector *)Xtmp3);
    xtmp1 = xTHbc * xsum;
    xtmp2 = xtmp1 - (l_real)13.5;
    Xtimesx((vector *)Xtmp2,xtmp2,(vector *)Xtmp1);
    Xdivx((vector *)Xtmp1,(l_real)100.0,(vector *)Xtmp3); /* save Xtmp3 */
    if(EnSlp == TRUE){ xtmp1 = (l_real)1.0; }
    else{          xtmp1 = (l_real)0.0; }
    Xtimesx((vector *)Xscat,xtmp1,(vector *)Xtmp1);
    xtmp2 = getXvalue((vector *)Xconc,6);
    Xtimesx((vector *)Xtmp1,xtmp2,(vector *)Xtmp2);
    XplusY((vector *)Xtmp2,(vector *)Xconc,(vector *)Xtmp1);
    xtmp3 = getXvalue((vector *)Xtmp1,4);
    xtmp2 = xtmp3 / xsum;
    if(xtmp2 > xsulfTHb){ int1 = 5; }
    else{          int1 = 4; }
    if(xtmp2 > xsulfslp){ xtmp2 = (l_real)0.0; }
    else{          xtmp2 = (l_real)1.0; }
    Xtimesx((vector *)Xsulf,xtmp1,(vector *)Xtmp4);
    Xtimesx((vector *)Xtmp4,xtmp2,(vector *)Xtmp2);
    Xtimesx((vector *)Xtmp2,xtmp3,(vector *)Xtmp4);
    XplusY((vector *)Xtmp1,(vector *)Xtmp4,(vector *)Xtmp2);
    Xsubset((vector *)Xtmp2,0,int1,(vector *)Xtmp1);
    xtmp3 = Xsum((vector *)Xtmp 1);
    Xdivx((vector *)Xtmp2,xtmp3,(vector *)Xtmp4);
    xtmp1 = Xtmp2[5];
    xtmp2 = xTHbc * xtmp1;
    Xtmp4[5] = xtmp2;   /* place value into vector */
    XplusY((vector *)Xtmp3,(vector *)Xtmp4,(vector *)Xsats);
    return;
} /* end slope_recur_LED( ) */
/* END FILE: MTX_COMP.C */
```

What is claimed is:

1. A method for quantitative hemoglobin determination in unaltered whole blood comprising:
   irradiating multiple wavelengths of light through a sample of unaltered whole blood; and
   using results of the irradiating in determining the concentration of hemoglobin in the sample, the determining including compensating for scattering.

2. A method for quantitative hemoglobin determination in unaltered whole blood comprising:
   providing a disposable cuvette;
   filling the cuvette with a sample of unaltered whole blood;
   irradiating multiple wavelengths of light through the sample; and
   using results of the irradiating in determining the concentration of hemoglobin in the sample, the determining including compensating for scattering.

* * * * *

UNITED STATES PATENT AND TRADEMARK OFFICE
CERTIFICATE OF CORRECTION

PATENT NO. : 7,075,628 B2  
APPLICATION NO. : 10/313220  
DATED : July 11, 2006  
INVENTOR(S) : Shepherd et al.

It is certified that error appears in the above-identified patent and that said Letters Patent is hereby corrected as shown below:

In the Title Page, item [57], Abstract, line 12, please delete "and shape" after "detector size".

In the Title Page, item [57], Abstract, line 15, after "scattering" please insert --and--.

Signed and Sealed this

Fifth Day of December, 2006

JON W. DUDAS  
*Director of the United States Patent and Trademark Office*